United States Patent
Eastman et al.

(10) Patent No.: US 10,137,105 B2
(45) Date of Patent: Nov. 27, 2018

(54) COMBINATION TREATMENT PROTOCOL

(71) Applicant: Bionomics Limited, Thebarton (AU)

(72) Inventors: Alan R. Eastman, Lebanon, NH (US); Darcy Bates, White River Junction, VT (US); Gabriel Kremmidiotis, Flagstaff Hill (AU)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 15/554,917

(22) PCT Filed: Mar. 2, 2016

(86) PCT No.: PCT/AU2016/050135
§ 371 (c)(1),
(2) Date: Aug. 31, 2017

(87) PCT Pub. No.: WO2016/138559
PCT Pub. Date: Sep. 9, 2016

(65) Prior Publication Data
US 2018/0042887 A1 Feb. 15, 2018

(30) Foreign Application Priority Data
Mar. 5, 2015 (AU) ................................ 2015900764

(51) Int. Cl.
*A61K 31/343* (2006.01)
*A61K 31/519* (2006.01)
*A61K 45/06* (2006.01)

(52) U.S. Cl.
CPC .......... *A61K 31/343* (2013.01); *A61K 31/519* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2011/0130367 A1* | 6/2011 | Kremmidiotis | A61K 31/343 514/100 |
| 2014/0248375 A1* | 9/2014 | Kremmidiotis | A61K 31/343 424/649 |

FOREIGN PATENT DOCUMENTS

| WO | WO 2011/022772 A1 | 3/2011 |
|---|---|---|
| WO | WO 2013/177633 A1 | 12/2013 |
| WO | WO 2015/149105 A1 | 10/2015 |
| WO | WO 2016/000012 A1 | 1/2016 |

OTHER PUBLICATIONS

International Search Report and Written Opinion for PCT/AU2016/050135, dated Mar. 23, 2016.
International Preliminary Report on Patentability for PCT/AU2016/050135, dated Sep. 14, 2017.
[No Author Listed] Wikipedia Entry—Ibrutinib, Available from the Internet, <URL:https://en.wikipedia.org/w/index.php?title=Ibrutinib&oldid=648994922>, Published Feb. 26, 2015 according to Wikipedia, Retrieved from the Internet Mar. 16, 2016. A See Heading "Medical Uses".
Bates et al., The microtubule-disrupting drug BNC105 is a potent inducer of acute apoptosis in CLL. Abstract 834. Proceedings of the 105th Annual Meeting of the American Association for Cancer Research;Apr 5-9, 2014. doi:10.1158/1538-7445.AM2014-834.
Flynn et al., Discovery of 7-hydroxy-6-methoxy-2-methyl-3-(3,4,5-trimethoxybenzoyl(benzo[b]furan (BNC105), a tubulin polymerization inhibitor with potent antiproliferative and tumor vascular disrupting properties. J Med Chem. Sep. 8, 2011;54(17):6014-27. doi: 10.1021/jm200454y. Epub Aug. 5, 2011.

* cited by examiner

*Primary Examiner* — Brian J Davis
(74) *Attorney, Agent, or Firm* — Wolf, Greenfield & Sacks, P.C.

(57) ABSTRACT

The present disclosure provides a combination and a method for treating chronic lymphocytic leukemia (CLL).

19 Claims, 12 Drawing Sheets

COMBINATION TREATMENT PROTOCOL

RELATED APPLICATIONS

This application is a national stage filing under 35 U.S.C. § 371 of international PCT application, PCT/AU2016/050135, filed Mar. 2, 2016, which claims priority to Australian patent application, AU 2015900764, filed Mar. 5, 2015, each of which is incorporated herein by reference.

BACKGROUND

Field

The present disclosure teaches a combination therapy for chronic lymphocytic leukemia (CLL).

Description of Related Art

Bibliographic details of the publications referred to by author in this specification are collected alphabetically at the end of the description.

Reference to any prior art in this specification is not, and should not be take as, acknowledgement or any form of suggestion that this prior art forms part of the common general knowledge in any country.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Cancer is typically treated with surgical, chemical and/or radiation ablation therapy. Whilst chemical and radiation ablation therapy is often effective to destroy a significant amount of tumor cells, such therapies often leave behind a number of tumor cells that are resistant to the treatment. These resistant cells can proliferate and/or metastasize to form new tumors that are or have the potential to become recalcitrant to treatment. Furthermore, the continuous use of chemotherapeutic drugs has given rise to drug resistant tumor cells. Even when combinations of drugs are employed, multidrug resistant (MDR) tumor cells can arise.

The American Cancer Society estimates there will be more" than 15,000 new cases and more than 4,500 deaths from chronic lymphocytic leukemia (CLL) in 2013 alone. Successful use of purine analogue-containing chemo-immunotherapy regimes extended survival of younger patients with CLL. However, eventual progression to fludarabine-resistant disease and lack of low-risk curative strategies warrant exploration of novel treatment strategies.

CLL is characterized by the accumulation of mature $CD5^+CD19^+CD23^+$ B lymphocytes in peripheral blood, bone marrow, lymph nodes and spleen, which is thought to be caused by a defect in the pathway to regulated cell death rather than an uncontrolled mechanism of cell proliferation. Such a defect can lead to chemoresistance and thus strategies are needed to lead to more potent therapeutics. The B-cell lymphoma/leukemia 2 (BCL-2) protein is over-expressed in CLL and, therefore, represents a target in attempts to overcome the resistance of tumors to anti-cancer treatments. CLL is a debilitating leukemia and, hence, there is an urgent need for selective treatments for this disease.

Introduction of the inhibitors of BCR-associated kinases has provided a great deal promise in targeted therapies in CLL. Ibrutinib, an inhibitor of BTK, resulted in an overall response rate of ~71% in a Phase Ib/II multicenter study in patients with relapsed/refractory CLL, a remarkable single drug activity. Complete remission was, however, rare (2.4%), and daily administration of the drug is typically required to maintain treatment efficacy. Monotherapy with BCR-targeting agents (including ibrutinib) led to the development of peripheral CLL cell lymphocytosis, which persisted for >12 months in 20% of patients. This may be a direct consequence of BCR inhibition-mediated egress of the neoplastic cells from their niche. Interestingly, in patients who received ibrutinib intermittently, the CLL cells were able to re-populate the lymph nodes during the off-time. Furthermore, reports of ibrutinib resistance due to mutations in the drug-binding cysteine residue in BTK have recently emerged. Other mechanisms of resistance may account for reduced efficacy of the BCR-targeting agents. For example, in vitro data suggest that upregulation of a PI3K isoform might rescue lymphoma cells from idelalisib, a PI3K-specific inhibitor. Thus, there is seen to be an increase in resistance to BCR-targeting agents, persistence of residual disease and the ability of CLL cells to re-populate their niche Accordingly, there is a need for a more efficacious and selective treatment of CLL.

SUMMARY

The present invention is predicated on the identification of CLL effective combination treatments which involve a compound of formula (I) and a compound that drives CLL cells from the lymph node or bone marrow.

In an embodiment the effective treatment for CLL involves the use of a combination of, in either order or simultaneously, a compound which induces CLL cell egress from lymph node or bone marrow, or a pharmaceutically acceptable salt, solvate, stereoisomer or prodrug thereof and a compound of Formula (I) or a pharmaceutically acceptable salt, solvate, or prodrug thereof. In an embodiment the effective treatment for CLL involves the use of a combination of, in either order or simultaneously, ibrutinib or a pharmaceutically acceptable salt, solvate, stereoisomer or prodrug thereof and a compound of Formula (I) or a pharmaceutically acceptable salt, solvate or prodrug thereof. In another embodiment the effective treatment for CLL involves the use of a combination of, in either order or simultaneously, idelalisib or a pharmaceutically acceptable salt, solvate, stereoisomer or prodrug thereof and a compound of Formula (I) or a pharmaceutically acceptable salt, solvate or prodrug thereof. In an embodiment the combination is useful in the treatment of patients with relapsed or refractory CLL or a CLL which is or has the potential of becoming recalcitrant to treatment.

As used herein "ibrutinib" refers to the compound of structure:

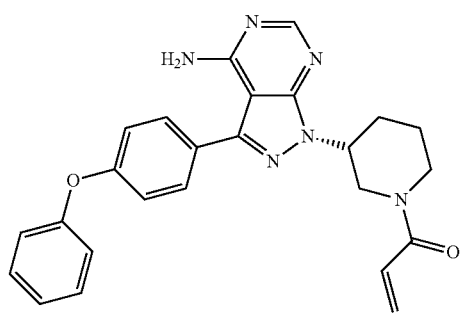

also known as PCI-32765 (Pharmacyclics) and marketed under the name Imbruvica. Its systematic (or IUPAC) name is 1-[(3R)-3-[4-Amino-3-(4-phenoxyphenyl)-1H-pyrazolo[3,4-d]pyrimidin-1-yl]piperidin-1-yl]prop-2-en-1-one and includes its pharmaceutically acceptable salt, solvate, stereoisomer and prodrug forms.

As used herein "idelalisib" refers to the compound of the structure:

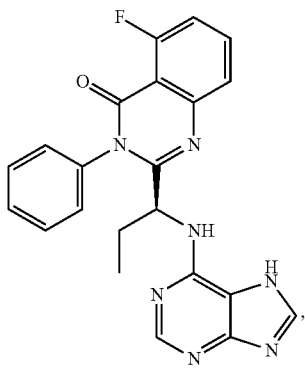 [SMILES: CC[C@H](Nc1ncnc2nc[nH]c12)c1nc2cccc(F)c2c(=O)n1-c1ccccc1]

also known as Zydelig, GS-1101 or CAL-101. Its systematic (or IUACC) name is 5-fluoro-3-phenyl-2[(1S)-1-7H-purin-6-ylamino)propyl]-4(3H)-quinazolinone; and includes its pharmaceutically acceptable salt, solvate, stereoisomer and prodrug forms.

The compound of Formula (I) is represented below:

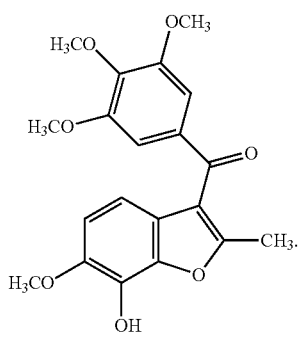

(I)

The compound of Formula (I) [2-Methyl-7-hydroxy-3-(3,4,5-trimethoxybenzoyl)-6-methoxybenzofuran] can be prepared by the synthetic methodology described in PCT/AU2007/000101 (WO 07/087684), the contents of which are incorporated by reference, and reference to the Formula (1) compound includes its pharmaceutically acceptable salt, solvate and prodrug forms.

Ibrutinib and idelalisib inhibit the pro-survival BCR signaling of CLL cells in the stomal niche resulting in their egress to the periphery. Importantly, if administration of ibrutinib or idelalisib is stopped, the CLL cells rapidly return to the lymph node. In some patients, the drug-induced increase in circulating CLL cells has been seen for more than a year reflecting the fact that the cells do not readily die once they exit the lymph node. Resistance to ibrutinib has been observed as mutations in the drug-binding cysteine in its target, BTK. Without wishing to be bound by theory, this resistance is likely to become far more prevalent as patients remain on ibrutinib for months or years. The present invention is predicated, in part, on the determination that certain CLL approved drugs which induce egress from lymph node or bone marrow will have far greater efficacy when they are combined with compounds of Formula (I) that kill the CLL cells in peripheral circulation, thereby preventing them from returning to the protective lymph node niche. Compounds of Formula (I) work through an entirely different mechanism, i.e. tipping the balance of pro-survival and pro-apoptotic BCL2 family member proteins toward the latter, resulting in cell death. This pathway of apoptosis occurs at all stages of the cell cycle which is important considering that the majority of peripheral CLL cells are non-cycling (in Go). The cells which leave the stromal niche following ibrutinib therapy will be susceptible to compounds of Formula (I) due to lack of additional pro-survival signals which emanate from stromal support.

Other compounds or drugs which induce egress of CLL cells from lymph node or bone marrow include: BTK inhibitors such as Acalabrutinib, ONO-4059, and spebrutinib (AVL-292, CC-292), or phosphoinositide 3-kinase inhibitors such as Perifosine, BKM120, Duvelisib, (IPI-145), PX-866, BAY 80-6946, BEZ235, RP6530, TGR 1202, SF1126, INK1117, GDC-0941, XL147 (also known as SAR245408), XL765 (also known as SAR245409), Palomid 529, GSK1059615, ZSTK474, PWT33597, IC87114, TG100-115, CAL263, RP6503PI-103, GNE-477, CUDC-907, and AEZS-136, or BCL-2 inhibitors such as venetoclax (ABT-199), ABT-737, or ABT-263, or CDK-inhibitors such as dinaciclib (SH-727965).

It is proposed herein that, in either order or simultaneously the compound of Formula (I) induces selected and preferential apoptosis of CLL cells via the JNK apoptotic pathway in combination with activating NOXA. It is for this proposed reason that only some microtubule drugs are effective in the treatment of certain leukemias. In accordance with the instant disclosure the compounds of Formula (I) are found effective against CLL cells facilitating their apoptosis.

Hence, enabled herein is a method of treating chronic lymphocytic leukemia (CLL) in a patient including the step of administering effective amounts of, at least two compounds, in either order or simultaneously, a compound which induces egress of CLL cells from lymph node or bone marrow or a pharmaceutically acceptable salt, solvate, stereoisomer or prodrug thereof, and a compound of Formula (I):

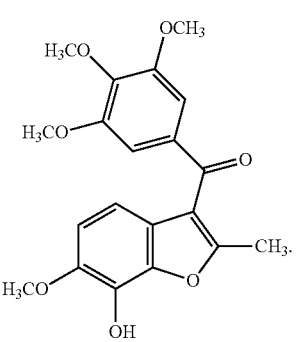

(I)

or a pharmaceutically acceptable salt, solvate or prodrug thereof.

In an embodiment the compound which induces egress of CLL cells from lymph node or bone marrow is ibrutinib or idelalisib. In an embodiment, the subject or patient is a human. In another embodiment, CLL is relapsed or refractory CLL. This may also be referred to as chronic, persistent or drug resistant CLL or a CLL recalcitrant to treatment.

In one aspect the present invention is predicated on the following strategy for effectively treating patients with CLL is adopted. Patients are administered a compound which induces egress of CLL cells from lymph node or bone marrow, driving the cells from the lymph node niche. Then a compound of Formula (I) is administered to kill the cells before they can return to the lymph nodes. In another aspect, the patient is given a compound of Formula (I) first followed by a compound which induces egress of CLL cells from lymph node or bone marrow, such as ibrutinib. In yet another aspect, both compounds are simultaneously administered.

Further taught herein is the use of ibrutinib or a pharmaceutically acceptable salt, solvate, stereoisomer or prodrug thereof and a compound of Formula (I):

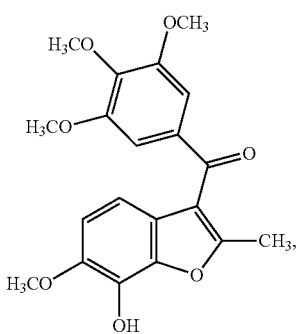

(I)

or a pharmaceutically acceptable salt, solvate or prodrug thereof in the manufacture of a medicament for treating a patient with chronic lymphocytic leukemia (CLL) including relapsed or refractory CLL. The medicament is intended to be used in a protocol to manage CLL therapy in a patient, the protocol comprising the combination of ibrutinib and a compound of Formula (1), in either order or simultaneously. In a further embodiment the medicament is a pharmaceutical composition comprising ibrutinib or a pharmaceutically acceptable salt, solvate, stereoisomer or prodrug thereof and a compound of Formula (I) or a salt, solvate or prodrug thereof.

The "pharmaceutical composition" may be a single composition or a combination composition of separate, distinct therapeutics maintained in a therapeutic kit or administered as part of a therapeutic protocol.

In a related embodiment, the present specification is instructive on a compound which induces egress of CLL cells from lymph node or bone marrow or a pharmaceutically acceptable salt, solvate, stereoisomer or prodrug thereof in combination with a compound of Formula (I):

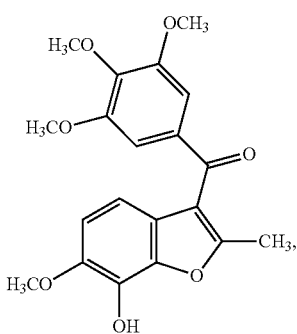

(I)

or a pharmaceutically acceptable salt, solvate or prodrug thereof; for use in treating CLL in a patient.

The present invention further provides a kit for the treatment of CLL comprising:
 (a) a compound which induces egress of CLL cells from lymph node or bone marrow or a pharmaceutically acceptable salt, solvate, stereoisomer or prodrug thereof;
 (b) an amount of a compound of Formula (1):

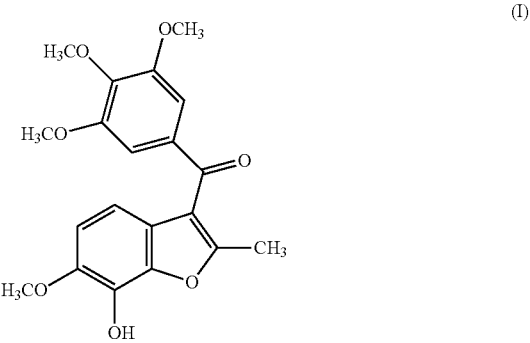 [SMILES: COc1cc(C(=O)c2c(C)oc3c(O)c(OC)ccc23)cc(OC)c1OC]

(I)

or a pharmaceutically acceptable salt, solvate or prodrug thereof; and
 (c) instructions for use of (a) and (b) in combination.

The instructions include use of the compound which induces egress of CLL cells from lymph node or bone marrow and Formula (1) in a therapeutic protocol to treat or manage CLL in a human subject. Either compound may be administered first or both be simultaneously administered. In an embodiment a compound which induces egress of CLL cells from lymph node or bone marrow is first administered.

In relation to the above embodiments, in a further embodiment the compound which induces egress of CLL cells from lymph node or bone marrow is ibrutinib.

In an embodiment, the instructions are directed specifically for treating relapsed or
refractory CLL in a human subject.

Without intending to be bound to any particular theory or mode of action, incubation with compounds of Formula (I) activates the JNK apoptotic pathway and upregulates functional Noxa in CLL cells at concentrations that cause cleavage of PARP and chromatin condensation. The Formula (1) compound's activity results in acute apoptosis of CLL cells. The effect of the compound of Formula (I) is achieved with an unexpectedly lower concentration than with other microtubule targeting drugs (i.e., increased potency). When incubated with CLL cells, vinblastine and combretastatin A4 show similar effects, but the compounds of Formula (I) are a more potent inducer of CLL activated pJNK and Noxa enabling greater levels of selective apoptosis of CLL cells. Furthermore, only a 1 h incubation is sufficient to activate JNK, and apoptosis is still observed 5 h after removal of a compound of Formula (I).

The instant specification teaches that apoptosis is dependent on the activation of JNK. Without limiting the present invention to any one theory or mode of action it is proposed herein that both Noxa and JNK are required for this acute apoptosis to occur in CLL cells. JNK is also activated in normal lymphocytes but in the absence of Noxa, were resistant to the compound of Formula (I).

Accordingly, in another embodiment the method involves initially treating a subject in need thereof with an effective amount of compound of Formula (I) in order to induce JNK-dependent apoptosis in CLL cells.

In an alternative embodiment, the method involves initially treating a subject in need thereof with an effective amount a compound which induces egress of CLL cells from lymph node or bone marrow, such as ibrutinib followed by a compound of Formula (I) in order to induce JNK-dependent apoptosis in CLL cells.

CLL cells are much more resistant to drugs when incubated with stroma cells that mimic the lymph node environment. Therefore, rational drug combinations are tested in an effort to circumvent this resistance. However the extent to which such combinations result in synergistic efficacy is limited. The compound of the present invention is able to induce apoptosis as a single agent through a mechanism that primarily involves BCL-2 and MCL-1 inhibition (FIG. 10). CLL cells grown on stroma are resistant to ABT-199 (a BCL-2 inhibitor), but are sensitized by compounds of the present invention. This sensitization is likely due to induction of Noxa. However, it is determined herein that the incubation with stroma cells also upregulates BCL-X which elicits resistance to Noxa induction. Since Noxa can also bind to BCL-X when present in excess over the binding capacity of MCL-1, this allows the combination to overcome the stroma-mediated chemoresistance of CLL cells.

Higher potency is a desired characteristic of a new drug because obviously a lower amount of drug is needed to assert an effect, but it can be detrimental if it is accompanied by higher toxicity or off target effects. The compounds of Formula (I) of the present invention do not have any toxic effects as a single agent in peripheral normal lymphocytes even when used at high concentration, comparable to those achievable in plasma. Activation of JNK but no PARP cleavage or Noxa induction is observed. The ability to act in synergy with ibrutinib enables much greater efficacy in a treatment of CLL in patients.

Reference to "CLL" includes its subtypes and its related forms including relapsed or refractory forms of CLL and other forms recalcitrant to treatment.

Reference to relapsed or refractory CLL refers to CLL which does not respond to single agent therapy and is encompassed under chronic and drug resistant CLL. This is also sometimes referred to as "relapse" meaning the return of the disease after some time in patients who were categorised as being in complete or partial remission.

DETAILED DESCRIPTION

Figure 1:
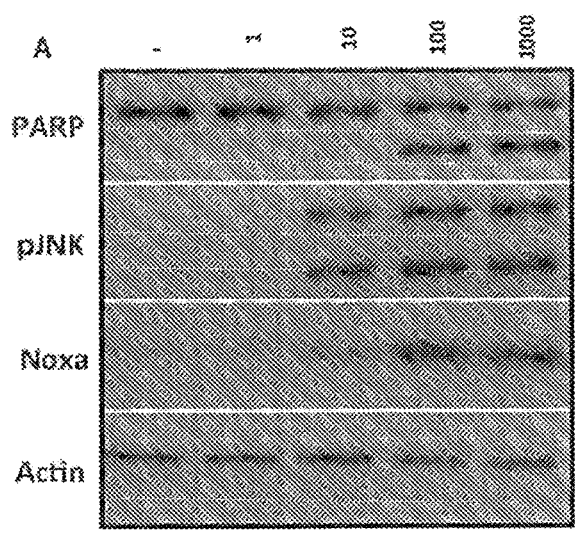
FIG. 1: Compounds of Formula (I) induce apoptosis in peripheral CLL cells. A) Western blots of CLL cells from patient incubated for 6 h with 0-1 μM compounds of Formula (I). B) Survival curve of the same CLL cells measured by chromatin condensation with Hoechst stain.
Figure 1:
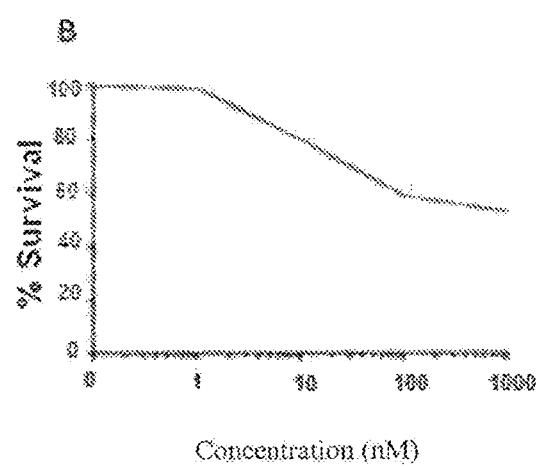

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in the subject specification, the singular forms "a", "an" and "the" include the plural aspects unless the context clearly dictates otherwise. Thus, for example, reference to "a CLL cell" includes a single cell, as well as two or more cells; reference to "an agent" includes a single agent, as well as two or more agents; reference to "the disclosure" includes a single and multiple aspects taught by the disclosure; and so forth. Aspects taught and enabled herein are encompassed by the term "invention". All such aspects are enabled within the width of the present invention.

The present disclosure teaches that certain compounds such as ibrutinib act in synergy with a compound of Formula (I) to effectively inhibit, control or otherwise clinically manage CLL in a patient. An important aspect of the compounds of Formula (I) is the combination of the specific C-6 and C-7 substituents together with the C-2 Q-group (especially C-2 methyl) which appears to confer greater potency and selectivity when compared to other structurally related TPI compounds. The compounds of Formula (I) show selectivity towards tumor endothelial cells (activated) over normal endothelial cells (quiescent).

It will be appreciated that ibrutinib may be administered as itself or in a form a pharmaceutically acceptable salt, solvate, stereoisomer or prodrug thereof. Similarly, a compound of Formula (I) can be administered to a subject as a pharmaceutically acceptable salt, solvate or prodrug thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric; tartaric, maleic, hydroxymaleic, fumaric, maleic, citric, lactic, mucic, gluconic, benzoic, succinic, oxalic, phenyl acetic, methanesulphonic, toluenesulphonic, benezenesulphonic, salicychc sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In an embodiment, the method described herein includes within its scope cationic salts e.g sodium or potassium salts, or alkyl esters (e.g. methyl, ethyl) of the phosphate group.

It will also be appreciated that any compound that is a prodrug of, for instance, ibrutinib or a compound of Formula (I) is also within the scope and spirit of the therapeutic protocol herein described. The term "pro-drug" is used in its broadest sense and encompasses those derivatives that are converted in vivo to a compound of the invention (for instance, ibrutinib or a compound of Formula (I)). Such derivatives would readily occur to those skilled in the art, and include, for example, in relation to Formula (1), compounds where the free hydroxy group (for instance at C-7 position or $R^{1D}$) is converted into an ester, such as an acetate or phosphate ester, or where a free amino group (for instance at C-7 position or $R^{1D}$) is converted into an amide (e.g., α-aminoacid amide). Procedures for esterifying, e.g. acylating, the compounds are well known in the art and may include treatment of the compound with an appropriate carboxylic acid, anhydride or chloride in the presence of a suitable catalyst or base. One prodrug is a disodium phosphate ester. The disodium phosphate ester (e.g., a C-7 disodium phosphate ester of a compound of formula I) of the compound of the present invention may be useful in increasing the solubility of the compounds. This would, for instance, may allow for delivery of the compound in a benign vehicle like saline. The disodium phosphate ester may be prepared in accordance with the methodology described in Pettit, et al, (1995) Anticancer Drug Des., 10:299. Other texts which generally describe prodrugs (and the preparation thereof) include: Bundgaard (1985) *Design of Prodrugs*, (Elsevier); Wermuth et al. (1996) *The Practice of Medicinal Chemistry*, Chapter 31 (Academic Press); and Bundgaard et al. (1991) *A Textbook of Drug Design and Development*, Chapter 5, (Harwood Academic Publishers).

Accordingly, in an embodiment the compound of Formula (I) is a compound represented as:

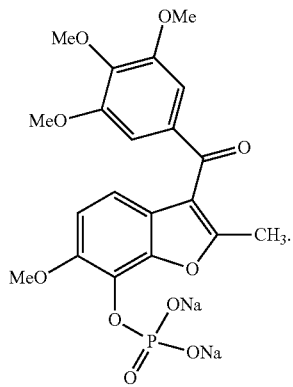

or a pharmaceutically acceptable salt, solvate or prodrug thereof.

The compounds of Formula (I) or a pharmaceutically acceptable salt, solvate or prodrug thereof) may be in crystalline form either as the free compound or as a solvate (e.g. hydrate) and it is intended that both forms are within the scope of the present invention. Methods of solvation are generally known within the art. Similar considerations apply to ibrutinib or its pharmaceutically acceptable salt, solvate, stereoisomer or prodrug.

An "effective amount" is intended to mean that the amount of a compound which induces egress of CLL cells from lymph node or bone marrow, such as ibrutinib or a pharmaceutically acceptable salt, solvate, stereoisomer or prodrug thereof, and a compound of Formula (I), or a salt, solvate or prodrug thereof and when administered to a subject in need of such treatment, is sufficient to effect treatment for CLL. This includes alleviating symptoms of CLL as well as inducing remission, delaying development of CLL and overall effective management of CLL in a patient. Thus, for example, a therapeutically effective amount is a quantity sufficient to reduce or alleviate CLL growth and development. An "effective dose" might require split dosing or cyclic dosing over a particular time interval. Hence, for example, if a particular amount is required to be administered over a 24 to 48 hour period within a cycle of treatment, this total amount might be delivered over 6 to 12 hourly intervals to reach the desired dosage per cycle. Any variation on split or cyclic dosing is encompassed herein. Split or intermittent dosing may involve cycles, for instance, of ibrutinib or a compound of Formula (I) use in a first cycle followed by the combination of the other of ibrutinib or a compound of Formula (I) in a subsequent cycle. A cycle may be for 7 to 30 days such as 21 days and from 3 to 20 cycles may be required such as about 6 cycles. However, the number of cycles required will depend on the severity of CLL, age of the patient, the overall health status of the patient and so on. A physician would be able to assess. Reference to a subject includes a human of any age. By being in need of such treatment includes patients suspected of having a high genetic or familial risk of developing CLL in an imminent time frame or patients with relapsed or refractory CLL or other recalcitrant CLL.

Treatment includes at least partially attaining the desired effect, or delaying the onset of, or inhibiting the progression of, or halting or reversing altogether the onset or progression of CLL.

In an embodiment, treatment is assessed by an amelioration of symptoms of CLL.

Clinical studies such as open-label, dose escalation studies in patients with CLL proliferative diseases are contemplated herein to identify synergism of ibrutinib and a compound of Formula (I). The beneficial and/or synergistic effects can be determined directly through the results of these studies which are known as such to a person skilled in the art. These studies are also able to compare the effects of a monotherapy using either ibrutinib or a compound of Formula (I) alone. In an embodiment, the dose of combination partner (a) may be escalated until the Maximum Tolerated Dosage (MTD) is reached, and agent (b) is administered as a fixed dose. Alternatively, combination partner (a) is administered in a fixed dose and the dose of agent (b) is escalated. Each patient may receive doses of agent (a) either daily, intermittently or cyclically. The efficacy of the treatment can be determined in such studies, e.g., after 6, 12, 18 or 24 weeks by evaluation of symptom scores every 9 weeks. In this embodiment one of partner (a) or agent (b) is considered one or both of ibrutinib or a compound of Formula (I) and the other of partner (a) or agent (b) is the other of ibrutinib or a compound of Formula (I).

The administration of the pharmaceutical combination of the present invention may result not only in a beneficial effect, e.g., an additive or synergistic therapeutic effect, for instance, with regard to alleviating, delaying progression of or inhibiting or ameliorating the symptoms of CLL, or refractory CLL, but also in further surprising beneficial effects. Such other effects may include fewer adverse side effects, an improved quality of life or a decreased morbidity, compared with a monotherapy applying only one of the pharmaceutically active ingredients used in the combination of the present invention.

A further benefit of the instant therapeutic protocol is that lower doses of the active ingredients of, for instance, ibrutinib and/or the compound of Formula (I) can be used. The dosages of each component (ibrutinib or a compound of Formula (I)) need not only be smaller but may also be applied less frequently, which may diminish the incidence or severity of side effects.

The treatment protocol herein described may further involve selecting a patient for treatment based on certain clinical parameters such as age, level of progression of the disease and/or other factors. In addition, patients are generally monitored for progression of CLL after initiation of treatment. Hence, after cessation of treatment, additional treatment may be required subsequently dependent on state or level of remission.

The term "administration" relates to the administration of ibrutinib or a pharmaceutically acceptable salt, solvate, stereoisomer or prodrug thereof, together with a compound of Formula (I), or a pharmaceutically acceptable salt, solvate or prodrug thereof, to a single patient. Combination therapy includes treatment regimens in which the agents are not necessarily administered by the same route of administration or at the same time. Accordingly, combination partners may be administered together, one after the other or separately in one combined unit dosage form or in two separate unit dosage forms. The unit dosage form may also be a fixed combination such as a pharmaceutical composition which comprises both partners or in separate doses in an intermittent or cyclic manner.

In an embodiment, a therapeutically effective amount of, for instance, ibrutinib may be administered alone or simultaneously or sequentially with a compound of Formula (I) and in any order, and the components may be administered separately or as a fixed combination. For example, the method of treating CLL or relapsed or refractory CLL according to the invention may comprise: (i) administration of a first combination partner in free or pharmaceutically acceptable salt, solvate, stereoisomer or prodrug form; and (ii) administration of a second combination partner in free or pharmaceutically acceptable salt, solvate, stereoisomer or prodrug form, simultaneously or sequentially in any order, in jointly therapeutically effective amounts, generally in synergistically effective amounts, e.g., in daily or intermittent dosages or in a cyclical regimen corresponding to the amounts described herein. Where a combination partner is ibrutinib, then a form of ibrutinib includes a stereoisomer thereof. The individual combination partners of the combination of the invention may be administered separately at different times during the course of therapy or concurrently in divided or single forms. The term administering also encompasses the use of a pro-drug of a combination partner that converts in vivo to the combination partner as such. The present invention is, therefore, to be understood as embracing all such regimens of simultaneous or alternating treatment and the term "administering" is to be accordingly interpreted.

In an embodiment, the one combination partner for administration is ibrutinib and another combination partner is a compound of Formula (I). In another embodiment, one combination partner is a compound of Formula (I) and the other combination partner is ibrutinib.

As such it will be appreciated that a combination of partners may be presented as a "kit of parts" or a "pharmaceutical kit" for use in the treatment of CLL. The kit may comprise a package where the combination partners are supplied separately for co-administration with instructions for use in the particular therapeutic regimen.

The effective dosage may vary depending on the particular compound or pharmaceutical composition employed, the mode of administration and the severity of CLL condition being treated. Thus, the dosage regimen is selected in accordance with a variety of factors including the route of administration and the renal and hepatic function of the patient. A physician of ordinary skill can readily determine and prescribe the effective amounts of each component in the combination required to alleviate, counter or arrest the progress of CLL.

Daily dosages will, of course, vary depending on a variety of factors, e.g., the compound chosen, the particular type of CLL to be treated and the desired outcome. In general, however, satisfactory results are achieved on administration of a compound of Formula (I) at daily dosage rates of about 0.05 to 20 mg/kg per day, particularly 1 to 20 mg/kg/per day, e.g. 0.4 to 16 mg/kg per day, as a single dose or in divided doses. As indicated above the dosage regimen per particular interval (e.g. 24 to 48 hours) may be split to achieve total dose over that period rather than bolus. The compound may be administered by any conventional route, in particular enterally, e.g., orally, e.g., in the form of tablets, capsules, drink solutions or parenterally, e.g., in the form of injectable solutions or suspensions. Suitable unit dosage forms for oral administration comprise from about 0.02 to 50 mg active ingredient, usually 0.1 to 30 mg and 2 to 25 mg, 4 to 20 mg, together with one or more pharmaceutically acceptable diluents or carriers therefore. Put in alternative terms the compound of Formular (I) may be provided in amounts of from 1 to 280 mg/m$^2$ per cycle. Ibrutinib may similarly be administered in amounts of about 200 to 800 mg per cycle.

An administration regime may include adding a compound of Formula (I) at an assigned dose level by iv on days 1 and 8 (of an at least 20 day cycle). In this embodiment the compound of Formula (I) may be dosed at a level of between 1 to 20 mg/m$^2$.

Administration of ibrutinib may include oral administration, e.g., orally, e.g., in the form of tablets, capsules, drink solutions or parenterally, e.g., in the form of injectable solutions or suspensions. Suitable unit dosage forms for oral administration comprise from about 200 to 800 mg daily, for instance, 480 mg daily.

In an embodiment, the compound of Formula (I) is given intravenously on days 1 and 8 at a first dose (approximately 1 to 8 mg/m$^2$ (e.g. 8 mg/m$^2$); cycle 1) followed by cycle 2 on days 8 and 15 at the same dose with 200 to 800 mg (e.g. 480 mg) daily ibrutinib. Cycle length is approximately 20 days, with 6 cycles required. Any number of cycles may be employed, depending on the response by the patient. Further, ibrutinib may be given as a first cycle followed by the compound of Formula (I).

The present invention also relates to pharmaceutical compositions which comprise compositions of ibrutinib and a compound of Formula (I) or salts, solvates, stereoisomers or prodrugs thereof, which for instance, contain, e.g., from about 0.1% to about 99.9% w/w or w/v, including from about 1% to about 50% w/w or w/v, of both ibrutinib and a compound of Formula (1).

The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In an embodiment unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Those skilled in the art will appreciate that the subject invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Synthetic Protocols

Preparation of 2-Bromo-7-acetoxy-3-(3,4,5-trimethoxybenzoyl)-6-methoxybenzofuran

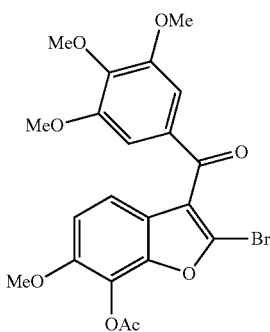 [SMILES: COc1cc(C(=O)c2c(Br)oc3c(OC(C)=O)c(OC)ccc23)cc(OC)c1OC]

Step 1: 2-t-Butyldimethylsilyl-3-(t-butyldimethylsilyloxymethylene)-6-methoxy-7-isopropoxybenzofuran (Larock coupling)

A suspension of 2-isopropoxy-3-methoxy-5-iodophenol (4.41 mmol), 1-(tert-butyldimethylsilyl)-3-(tert-butyldimethylsilyloxy)propyne (1.5 g, 5.28 mmol), lithium chloride (189 mg, 4.45 mmol) and sodium carbonate (2.34 g, 22.08 mmol) in dry dimethylformamide (5 mL) at 100° C. was deoxygenated 4 times by evacuation and backfilling with nitrogen. Palladium acetate (135 mg, 0.60 mmol) was added and the reaction vessel was degassed twice with nitrogen. The reaction mixture was then stirred at this temperature for 4 hours (tlc) and the solvent was removed by distillation under vacuum. The residue was dissolved in ethyl acetate (75 mL), stirred well, filtered and treated with triethylamine (5 mL). The solution was concentrated onto silica gel (10 g) and purified by flash chromatography (silica gel, eluent=hexane/diethyl ether/triethylamine; 95:5:1%) to afforded the title compound as a yellow oil (1.45 g, 96%); $^1$HNMR (300 MHz, CDCl$_3$) δ 7.24 (d, 1H, J=8.45 Hz), 6.88 (d, 1H, J=8.47 Hz), 4.80 (s, 2H, CH$_2$), 4.73 (m, 1H), 3.88 (s, 3H, OMe), 1.36 (d, 6H, J=6.17 Hz), 0.94 (s, 9H), 0.92 (s, 9H), 0.35 (s, 6H), 0.12 (s, 6H).

Step 2: 2-t-Butyldimethylsilyl-3-formyl-6-methoxy-7-isopropoxybenzofuran

To a solution of 2-t-butyldimethylsilyl-3-(t-butyldimethylsilyloxymethylene)-6-methoxy-7-isopropoxybenzofuran (2.69 mmol) in methanol (100 mL) was added concentrated hydrochloric acid (200 μL) and the reaction was stirred for 30 minutes (monitored by tlc), quenched with triethylamine (2 mL) and the solvent removed by distillation under vacuum. The residue was dissolved in dichloromethane (20 mL), washed with water (10 mL), dried over magnesium sulfate, concentrated under vacuum and co-distilled with toluene (20 mL). The crude product was dissolved in dry dichloromethane (4 mL) and added to a stirred solution of Collin's reagent (chromium trioxide (1.01 g), pyridine (1.65 mL) in dry dichloromethane (30 mL)). The suspension was stirred for 10 minutes, filtered and the residue washed with diethyl ether (20 mL). The filtrate was concentrated onto silica (10 g) and purified by flash chromatography (silica gel, eluent=hexane/diethyl-ether/triethylamine (90:9:1) to afford the title compound as a light yellow oil (503 mg, 48%); $^1$H NMR (300 MHz, CDCl$_3$) δ 10.25 (s, 1H, CHO), 7.79 (d, 1H, J=8.45 Hz), 6.98 (d, 1H, J=8.46 Hz), 4.65 (m, 1H), 3.89 (s, 3H, OMe), 1.35 (d, 6H, J=6.17 Hz), 0.97 (s, 9H), 0.45 (s, 6H).

Step 3: 2-t-Butyldimethylsilyl-3-(3,4,5-trimethoxybenzoyl)-6-methoxy-7-isopropoxybenzofuran To a stirred solution of 3,4,5-trimethoxyiodobenzene (377 mg, 1.27 mmol) in dry tetrahydrofuran (1 mL) at −78° C. under nitrogen was added n-butyllithium (795 μL, 1.59 mmol, 2M solution in cyclohexane) and the reaction mixture was stirred at this temperature for 40 minutes. After this time a solution of 2-t-butyldimethylsilyl-3-formyl-6-methoxy-7-isoproxybenzofuran (1.07 mmol) in dry tetrahydrofuran (1 mL) was added to the reaction dropwise via syringe pipette. The reaction mixture was stirred at −60° C. for 20 minutes and then allowed to warm to 0° C., stirred for 10 minutes, quenched with saturated ammonium chloride solution (2 mL) and diluted with ethyl acetate (20 mL). The organic layer was washed with water (10 mL), dried over magnesium sulfate and the solvent was removed under vacuum to give a residue that was co-distilled with toluene. The crude product (908 mg) was dissolved in dry tetrahydrofuran (10 mL) and treated with 2,3-dichloro-5,6-dicyano-1,4-benzoquinone (900 mg, 1.59 mmol) was added. The reaction mixture was stirred at room temperature for 16 hours (monitored by tlc) and then loaded onto silica (10 g) and purified by flash chromatography (silica gel, eluent=hexane/diethyl ether/triethylamine, 90:9:1) to afford the title compound as a light yellow oil (498 mg, 69%); $^1$H NMR (300 MHz, CDCl$_3$) δ 7.14 (s, 2H, benzoyl Hs), 6.81 (d, 1H, J=8.64 Hz), 6.77 (d, 1H, J=8.64 Hz) 4.74 (m, 1H), 3.93 (s, 3H, OMe), 3.86 (s, 3H, OMe), 3.78 (s, 6H, 2×OMe), 1.39 (d, 6H, J=6.14 Hz), 1.01 (s, 9H), 0.26 (s, 6H).

Step 4: 2-(tert-butyldimethylsilyloxy)-7-acetoxy-3-(3,4,5-trimethoxybenzoyl)-6-methoxybenzofuran To a stirred solution of 2-(t-butyldimethylsilyloxy)-7-isopropoxy-3-(3,4,5-trimethoxybenzoyl)-6-methoxy-benzofuran (160 mg, 0.31 mmol) in dry DCM (2 mL) at room temperature under nitrogen was added solid aluminium trichloride (83 mg, 0.62 mmol) and the reaction mixture was stirred for 15 minutes (monitored by tlc). The reaction was quenched with a saturated solution of ammonium chloride, extracted with dichloromethane and dried over magnesium sulfate. The solvent was removed by distillation and residue was dried by azeotropic removal of water with toluene. The crude product was dissolved in pyridine (2 mL), acetic anhydride (1 mL) was added and reaction mixture was stirred for 2 hours at room temperature. The solvent was distilled under vacuum and the residue was loaded onto silica gel (1 g) and purified by column chromatography (silica gel, eluent, hexane:diethyl-ether; 80:20) (134 mg, 84%); $^1$H NMR (300 MHz, CDCl$_3$) δ 7.14 (s, 2H, benzoyl Hs), 6.98 (d, 1H, J=8.72 Hz), 6.85 (d, 1H, J=8.72 Hz), 3.93 (s, 3H, OMe), 3.86 (s, 3H, OMe), 3.80 (s, 6H, 2×OMe), 2.41 (s, 3H), 0.99 (s, 9H), 0.25 (s, 6H).

Step 5: 2-Bromo-7-acetoxy-3-(3,4,5-trimethoxybenzoyl)-6-methoxybenzofuran

To a stirred solution of 2-t-butyldimethylsilyl-7-acetoxy-3-(3,4,5-trimethoxybenzoyl)-6-methoxybenzofuran (120 mg, 0.44 mmol) in 1,2-dichloroethane (1 mL) at room temperature under nitrogen was added bromine (12 μl, 0.44 mmol) dropwise and the reaction mixture was stirred at this temperature for 10 minutes. After this time the reaction was quenched with saturated sodium thiosulfate solution, extracted with ethyl acetate (20 mL), dried over magnesium sulfate and the solvent removed by distillation under vacuum. The crude product was purified by silica gel column chromatography (eluent=Hexane:diethyl ether; 8:2-7:3) to afford the title compound as a colourless crystalline solid (91 mg, 81%); $^1$H NMR (300 MHz, CDCl$_3$) δ 7.40 (d, 1H, J=8.70 Hz), 7.14 (s, 2H, benzoyl-Hs), 6.98 (d, 1H, J=8.75 Hz), 3.94 (s, 3H, OMe), 3.89 (s, 3H, OMe), 3.86 (s, 6H, 2×OMe), 2.43 (s, 3H); $^{13}$C NMR (75 MHz, CDCl$_3$) δ 187.95 (CO), 167.71, 152.75, 149.54, 147.49, 142.59, 131.92, 131.80, 123.91, 121.84, 119.89, 117.72, 109.89, 106.92, 60.69, 56.61, 56.00, 20.09.

Example 1

Preparation of 2-Methyl-7-hydroxy-3-(3,4,5-trimethoxybenzoyl)-6-methoxybenzofuran

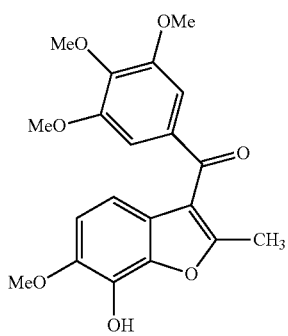 [SMILES: COc1cc(C(=O)c2c(C)oc3c(O)c(OC)ccc23)cc(OC)c1OC]

Preparation A

To a stirred solution of 2-Bromo-7-acetoxy-3-(3,4,5-trimethoxybenzoyl)-6-methoxybenzofuran (20 mg, 0.042 mmol), methyl-boronic acid (40 mg, 0.67 mmol), in 1,4-dioxane (2 mL) at 90° C. was added tetrakis-triphenylphosphine palladium (11 mg, 0.01 mmol) followed by the addition of a solution of sodium bicarbonate (40 mg, 0.48 mmol) in distilled water (0.5 mL). The reaction mixture turned red after 5 minutes. After 2 hours (tlc) the reaction mixture was brought to room temperature and was added saturated ammonium chloride (2 mL) and diluted with dichloromethane (20 mL). The organic layer was separated and washed with water, dried over magnesium sulfate and the solvent was removed by distillation under vacuum. The residue was purified by PTLC (eluent=Dichloromethane/Methanol, 1:1) to give the title compound (acetate cleaved during reaction) as a fluffy white solid; (3 mg, 19%).

Preparation B (Negishi Coupling)

To a stirred solution of zinc-bromide (592 mg, 2.63 mmol) in dry THF (1.5 mL) at 0° C. was added the solution of methyl lithium (1.6 M solution in diethyl-ether, 2.6 mL, 4.15 mmol) and the reaction mixture was stirred for 2 hours. Solid 2-bromo-7-acetoxy-3-(3,4,5-trimethoxybenzoyl)-6-methoxy-benzofuran (300 mg, 0.63 mmol) was added and the ether was removed under vacuum and to the rest suspension was added dichlorobis(triphenylphosphine)palladium catalyst (21 mg) and catalytic amount of copper (I) iodide. The reaction mixture was stirred at room temperature for 36 hours (monitored by tlc), quenched with saturated ammonium chloride solution and extracted with dichloromethane (10 mL), dried over magnesium sulfate and solvent distilled under vacuum and the product was purified by silica gel column (eluent=hexane/ethyl acetate; 8:2). The product was crystallized in methanol (106 mg, 46%); $^1$H NMR (300 MHz, CDCl$_3$) δ 7.09 (s, 2H, benzoyl Hs), 6.93 (d, 1H, J=8.54 Hz), 6.83 (d, 1H, J=8.56 Hz), 5.70 (bs, 1H, OH), 3.93 (s, 3H, OMe), 3.92 (s, 3H, OMe), 3.83 (s, 6H, 2×OMe), 2.54 (s, 3H, 2-Me)

Example 2

Preparation of Disodium 6-methoxy-2-methyl-3-(3,4,5-trimethoxybenzoyl)benzofuran-7-yl phosphate

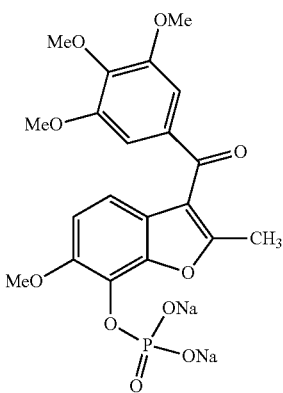

Step 1: Dibenzyl 6-methoxy-2-methyl-3-(3,4,5-trimethoxybenzoyl)benzofuran-7-yl phosphate To a mixture of 0.081 g (0.22 mmol) of (7-hydroxy-6-methoxy-2-methylbenzofuran-3-yl)(3,4,5-trimethoxyphenyl)methanone, 0.086 g (0.261 mmol) of carbon tetrabromide and 0.063 ml (0.283 mmol) of dibenzylphosphite in 2.5 ml of anhydrous acetonitrile 0.046 ml of anhydrous triethylamine was added dropwise at 0° C. under nitrogen atmosphere. The resulting mixture was stirred for 2 h at room temperature, then diluted to 20 ml with ethyl acetate, washed with water brine, dried over anhydrous magnesium sulfate, filtered off and evaporated to dryness under reduced pressure. The residue was purified by flash column chromatography (dichloromethane/ethyl acetate, 9:1) to give the title compound as a colorless foam (0.13 g, 94%); $^1$H NMR (CDCl$_3$) δ 2.42 (s, 3H, Me-2); 3.83 (s, 1H, OMe); 3.93 (s, 3H, OMe); 5.33 (m, 4H, CH$_2$Ph); 6.89 (d, CH aromatic, J=8.7 Hz); 7.21 (dd, 1H, CH aromatic, J=8.72 Hz; J-1.2 Hz); 7.08 (s, 2H, CH aromatic); 7.29-7.43 (m, 10H, CH aromatic).

Step 2: Disodium 6-methoxy-2-methyl-3-(3,4,5-trimethoxybenzoyl)benzofuran-7-yl phosphate To a stirred solution of 0.122 g (0.193 mmol) of the product from Step 1 in 1 ml of anhydrous acetonitrile 0.075 ml (0.58 mmol) of bromotrimethylsilane was added at −5° C. under nitrogen atmosphere. The resulting mixture was stirred for 1 h at 0° C., then evaporated to dryness in vacuo. The residue was diluted to 5 ml with anhydrous methanol and pH of the solution was brought up about 10 by the addition of sodium methoxide. After evaporation of the resulting mixture under reduced pressure the solid residue was washed with anhydrous isopropanol (4×1.5 ml) and anhydrous ethanol (3×1.5 ml) and dried under vacuum to give 0.062 g (65% yield) of title compound as an colorless solid; $^1$H NMR (D$_2$O) δ 2.37 (s, 3H, Me-2); 3.76 (s, 6H, OMe); 3.79 (s, 3H, OMe); 3.82 (s, 3H, OMe); 4.66 (s, H$_2$O); 6.93 (d, 1H, CH aromatic, J=8.6 Hz); 7.04 (d, 1H, CH aromatic, J=8.6 Hz); 7.10 (s, 211, CH aromatic).

Biological Data

Materials and Methods

Reagents

Example 2 (EX2) used in these studies was obtained from Bionomics Ltd. ABT-199 was purchased from Active Biochem. Dinaciclib was obtained from the Cancer Therapy Evaluation Program, National Cancer Institute. c-Jun-NH2-terminal kinase (JNK) inhibitor VIII was purchased from Calbiochem. Hoechst 33342 was purchased from Molecular Probes. Vinblastine, combretastatin A and other reagents were purchased from Sigma.

The following antibodies were used: phospho-c-Jun (Ser-63; 9261), phospho-JNK1/2 (9255), JNK1/2 (9252), and poly ADP ribose polymerase (PARP; 9542; Cell Signaling); Noxa (OP180) and actin (EMD Biosciences; JLA20). Secondary antibodies were purchased from BioRad.

Cell Culture

CLL cells were obtained from consented patients at the Norris Cotton Cancer Center. Cells were purified by centrifugation in Ficoll-Paque PLUS from 10 mL of blond. Lymphocytes were plated in RPMI 1640 plus 10% serum at 1×10$^6$ cells/mL after three washes in PBS+2 mmol/L EDTA. Cells were either incubated immediately with reagents or after 24 h incubation with confluent layers of CD154+ stromal cells (L 4.5) at a ratio of 5:1.

Chromatin Staining

Cells were incubated for 10 mm with 2 μg/mL Hoechst 33342 at 37° C. and visualized with a fluorescent microscope. At least 200 cells were scored for each sample. The percentage of cells with condensed chromatin was recorded.

Immunoblot Analysis

Cells were lysed in urea sample buffer [4 mol/L urea, 10% β-mercaptoethanol, 6% w/v SDS, 125 mmol/L Tris (pH 6.8), 0.01% w/v bromphenol blue, and protease/phosphatase inhibitor cocktail] and boiled for 5 min. Proteins were subsequently separated by SDS-PAGE (10 or 15% w/v) and transferred to polyvinylidene difluoride membrane (Millipore). Membranes were blocked with 5% w/v nonfat milk in TBS and 0.05% w/v Tween 20, and were probed with the appropriate primary antibody overnight. Subsequently, membranes were washed in TBS and 0.05% w/v Tween 20, and then incubated with secondary antibody conjugated to horseradish peroxidase. Proteins were visualized by enhanced chemiluminescence (Amersham). Actin was used as a loading control in Western blots.

Results

Single Agent Efficacy of EX2 in CLL Cells

To determine whether EX2 induces apoptosis, freshly isolated CLL cells were incubated in media containing 0-1 μM EX2. Chromatin condensation was scored as a classic marker of apoptosis. Apoptosis was observed following incubation of cells with 10-100 nM EX2 and this also correlated with the cleavage of PARP (FIG. 1). Protein lysates were also assessed for both pJNK and NOXA, both of which were increased by the same concentrations of EX2.

Figure 2:
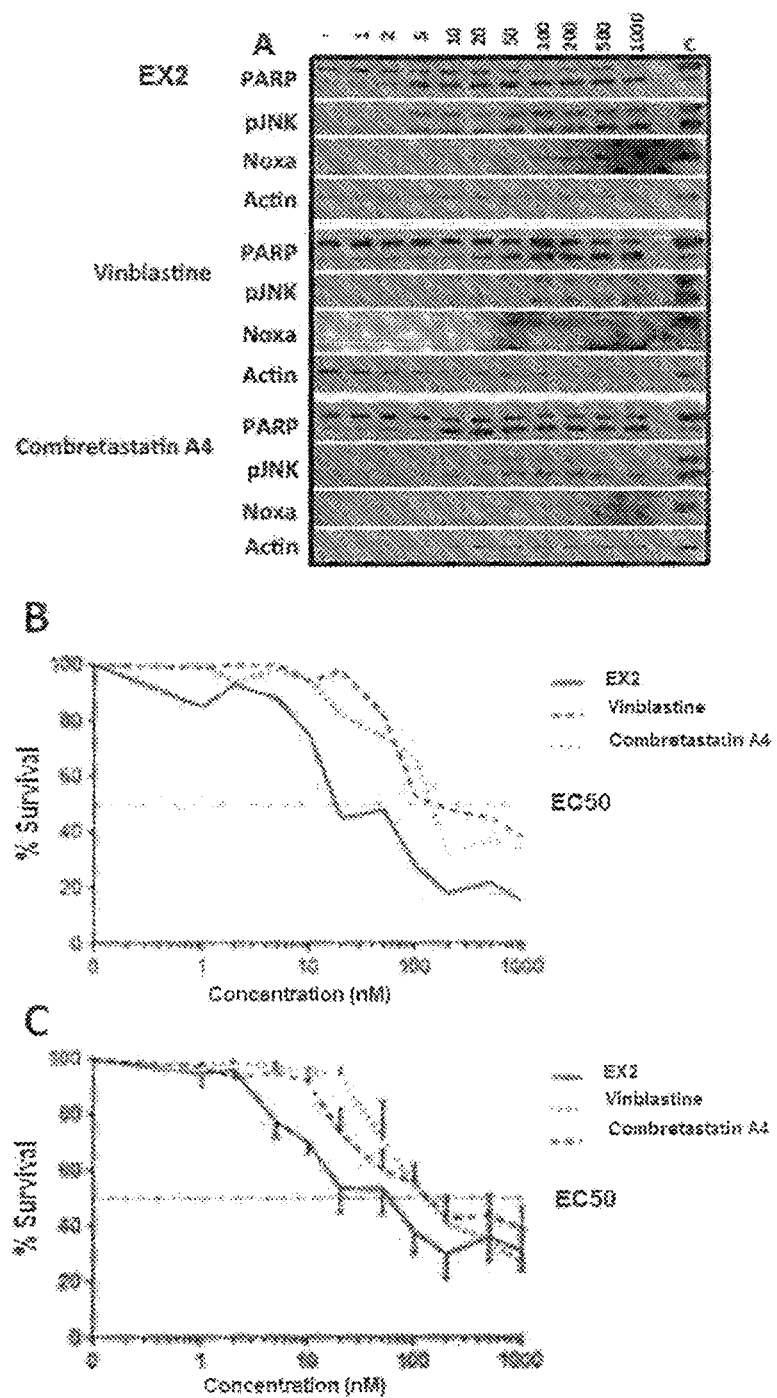
FIG. 2: Compounds of Formula (I) are the more potent apoptosis inducer in CLL cells. A) Western blots of CLL cells from patient 49 incubated for 6 h with 0-1 μM compounds of Formula (I), vinblastine or combretastatin A4. "C"=a control cell line incubated with 2 μM vinblastine as a positive control for protein expression. B) Survival curve of the same CLL cells measured by chromatin condensation with Hoechst stain. C) Comparison of the survival curves of CLL cells from 3-6 patients incubated for 6 h with a compound of Formula (I), vinblastine or combretastatin A4 (Mean+/−SEM).

The efficacy of three microtubule disrupting agents, EX2, vinblastine and combretastatin A4 was the compared, in greater detail. FIGS. 2A and B reflect one individual patient, while FIG. 2C reflects an average of 3-6 patients. EX2 is the more potent inducer of apoptosis in CLL cells, as assessed by both chromatin condensation and PARP cleavage. In each case, pJNK and Noxa expression correlated with the appearance of apoptosis, which in the case of EX2 began to appear at concentrations as low as 5 nM (FIG. 2A).

Apoptosis Induced in CLL Cells is JNK Dependent

Figure 3:
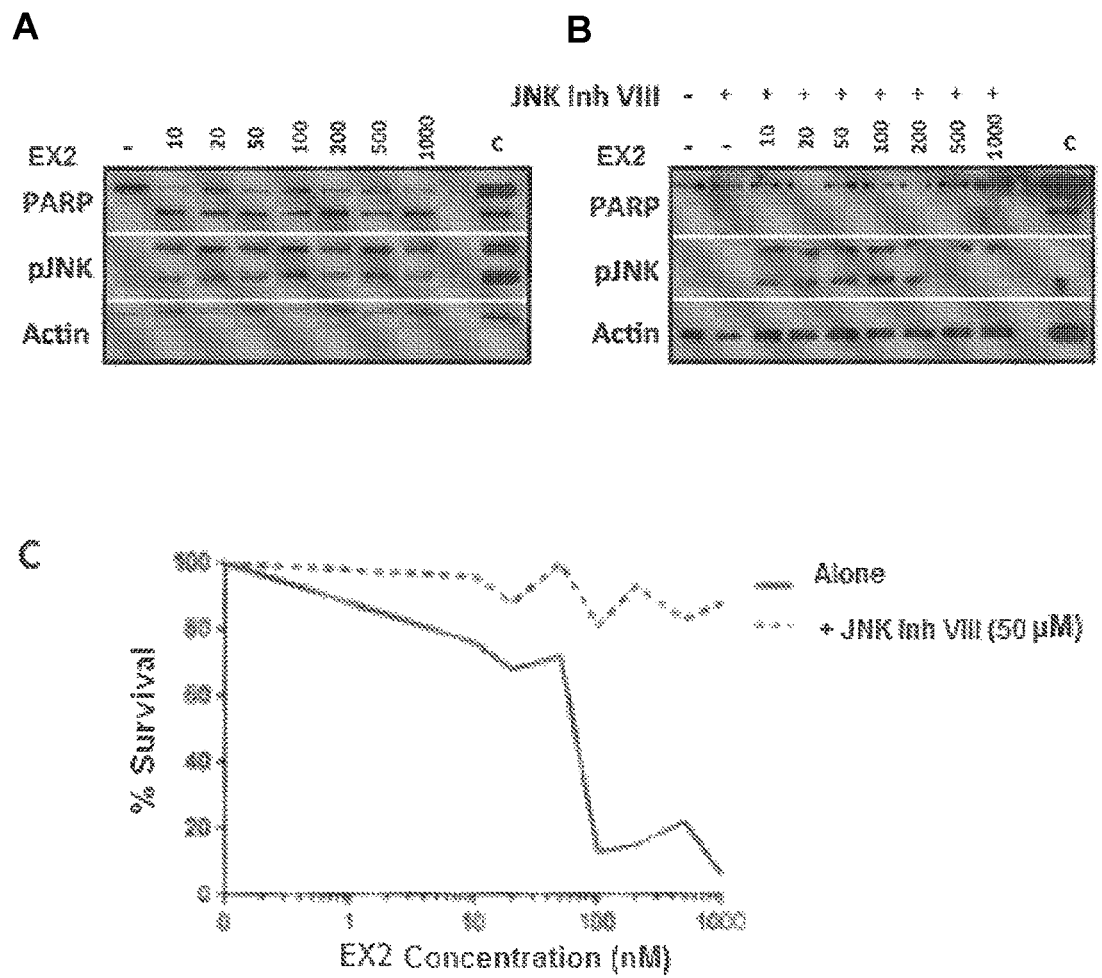
FIG. 3: Compounds of Formula (I)-induced apoptosis in CLL cells is JNK dependent A) Western blots of CLL cells from patient 15 incubated for 6 h with 0-1 μM compounds of Formula (I) (10-1000 nM). "C"=a control cell line incubated with 2 μM vinblastine as a positive control for protein expression. B) Parallel incubations were performed but in the presence of JNK inhibitor VIII. C) Survival curve of the same CLL cells measured by chromatin condensation.

CLL cells were incubated with 0-1 μM EX2 in the presence or absence of the JNK inhibitor VIII. PARP cleavage is seen in the absence of the inhibitor but is completely prevented by the JNK inhibitor (FIGS. 3A, B, and 10A, B), and this correlates with the observed cell survival measured by condensed chromatin staining (FIG. 3C). Phosphorylated JNK is observed in all conditions with and without the inhibitor. These results suggest that the mechanism leading to apoptosis induced by EX2 in CLL cells is dependent on pJNK activity.

Figure 4:
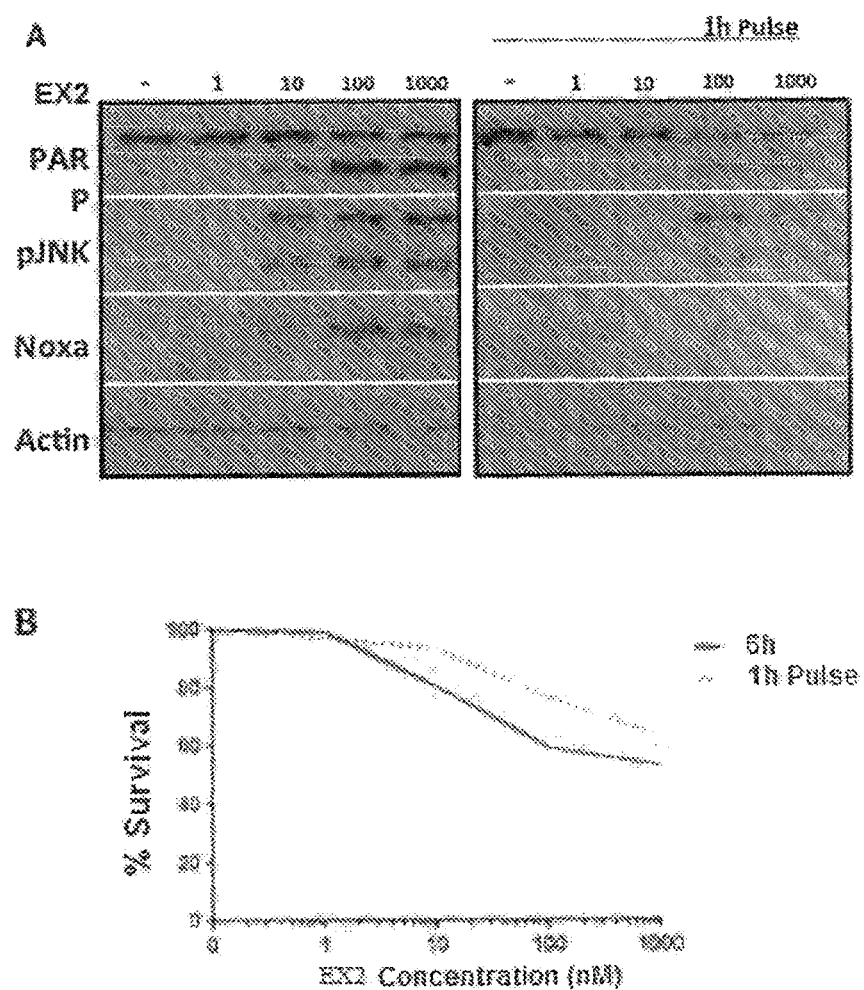
FIG. 4: Compounds of Formula (I) induce apoptosis after 1 h pulse incubation in CLL cells. A) Left: Western blots of CLL cells from patient 66 incubated for 6 h with 0-1 μM compounds of Formula (I) (1-1000 nM). Right: The same cells were incubated with compounds of Formula (I) for 1 h, then in the absence of media for an additional 5 h. B) Survival curve of the same CLL cells measured by chromatin condensation assay with Hoechst stain.

The activation of JNK occurs rapidly (in less than one hour). It was then determined whether a 1 h pulse treatment with EX2 would be as effective as a continuous incubation with EX2. Five hours after removing EX2, JNK activation and PARP cleavage were still observed albeit slightly less than when the EX2 was incubate with the cells continuously (FIG. 4).

Figure 5:
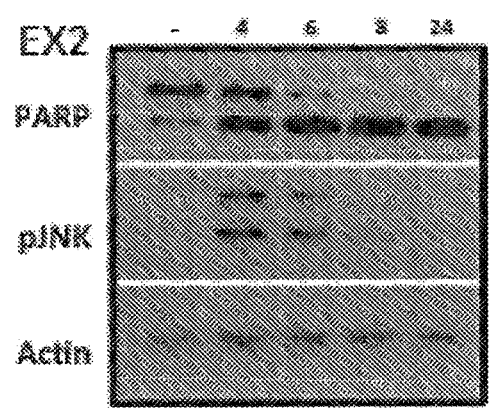
FIG. 5: Kinetics of compounds of Formula (I)-induced apoptosis in CLL cells. Western blots of CLL cells from patient 114 incubated with 20 nM compounds of Formula (I).
Figure 6:
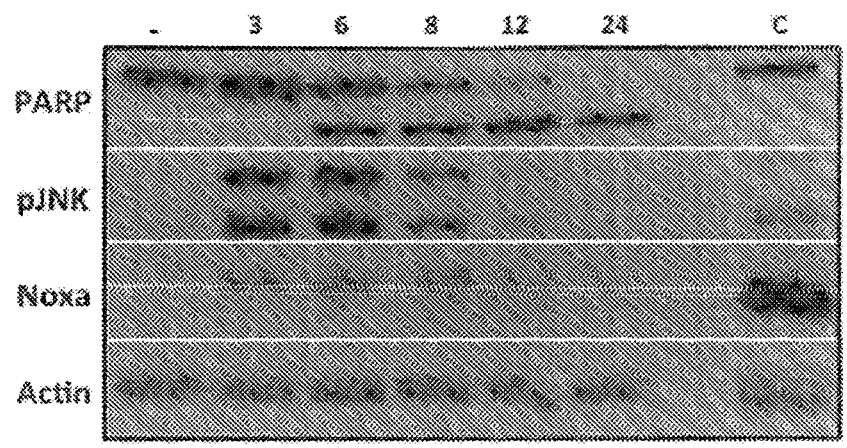
FIG. 6: Kinetics of compounds of Formula (I) induced apoptosis in Jeko-1 cells. Western blots of Jeko-1 cells incubated with 20 nM compounds of Formula (I). "C"=a control cell line incubated with 2 μM vinblastine as a positive control for protein expression.

It was noted that in many of these experiments, PARP cleavage was incomplete at 6 h. To determine whether greater apoptosis occurred at later time points, we incubated cells for up to 24 h with EX2 (FIG. 5). Apoptosis increased over this time frame with almost total cleavage of PARP observed by 24 h, albeit the example shown appears to be particularly sensitive to EX2 even at 6 h. However, in a parallel experiment using Jeko-1 cells, it was found that the majority of apoptosis occurred between 6 and 12 h and was complete by 24 h (FIG. 6). Hence it appears that apoptosis is not restricted to any subpopulation but can occur in the entire population of cells.

Figure 7:
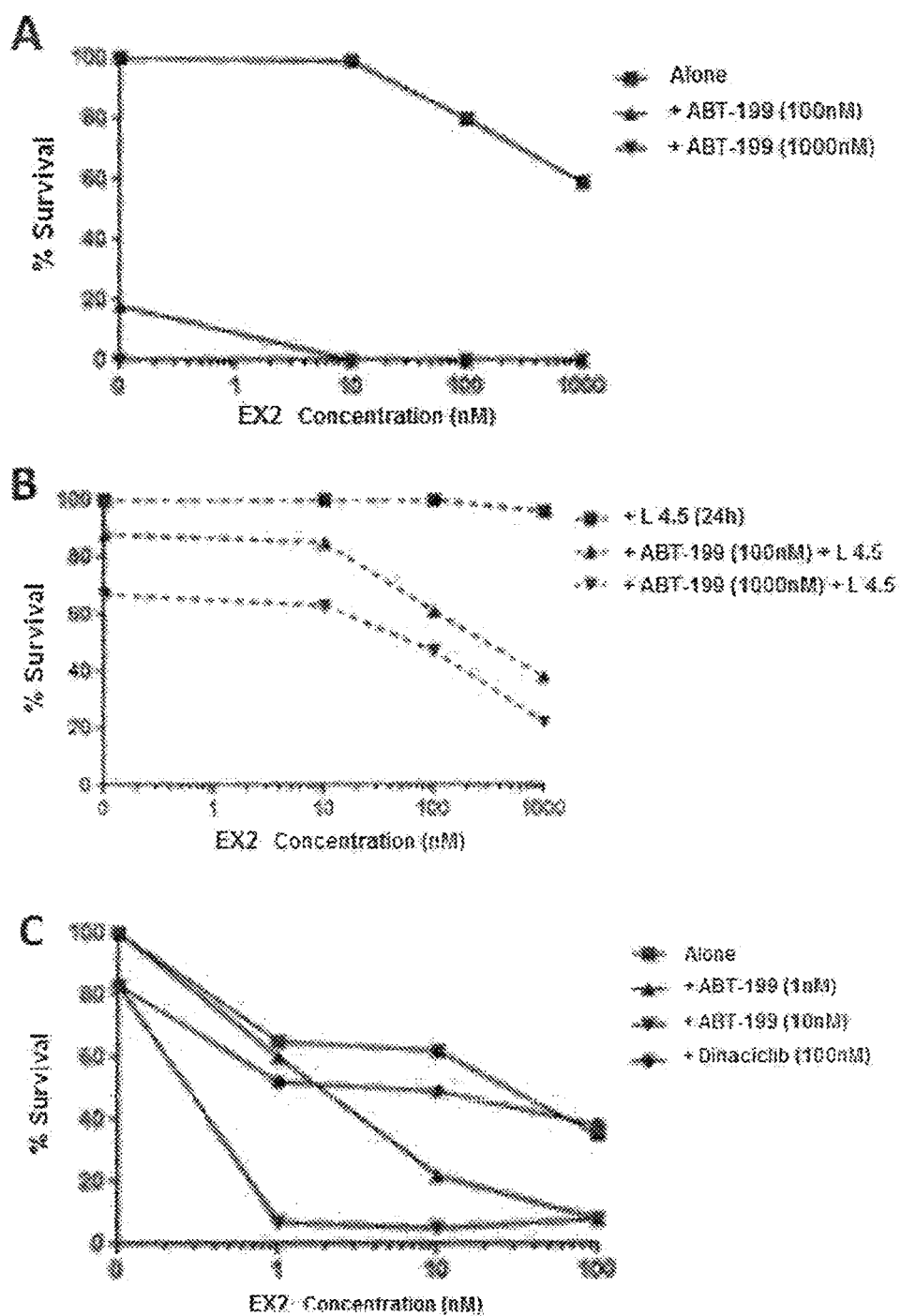
FIG. 7: Compounds of Formula (I) sensitize peripheral CLL cells to ABT-199 incubated on stroma. A) Survival curves of the CLL cells from patient 66 incubated with compounds of Formula (I) alone, or in combination with ABT-199. B) The CLL cells were incubated for 24 h on L4.5 stromal cells, then incubated with compounds of Formula (I) alone or in combination with ABT-199 for 6 h. C) Similar to A except performed on cells from patient 125.

Stroma Mediates Resistance to EX2 which can be Circumvented by Novel Drug Combinations The experiments above have shown that CLL cells are usually very sensitive to EX2. However, these cells were isolated from peripheral blood, and the real problem to curing CLL is to be able to kill cells that reside in the lymph node or bone marrow niche. To mimic this niche, we have used L4.5 cells that express CD154. Co-incubation of CLL cells on this stroma for 24 h elicits marked resistance to many drugs including the BCL-2 inhibitor ABT-199 (FIG. 7). These co-cultured CLL cells are also markedly resistant to EX2 with no apoptosis observed at 1 µM (FIG. 7). However, when ABT-199 and EX2 were combined, marked apoptosis was again observed. For example, 100 nM ABT-199 alone induced about 10% apoptosis, whereas when combined with 1 µM EX2, >60% apoptosis was observed within 6 h. The combination of 1 µM EX2 and 1 µM ABT-199 induced about 80% apoptosis. This patient's cells appeared to be more resistant than those summarized in FIG. 2 which may therefore understate the impact of this combination. In cells from another patient that were more sensitive to EX2 alone a greater sensitization to ABT-199 was observed.

Normal Peripheral Lymphocytes are Resistant to EX2

Figure 8:
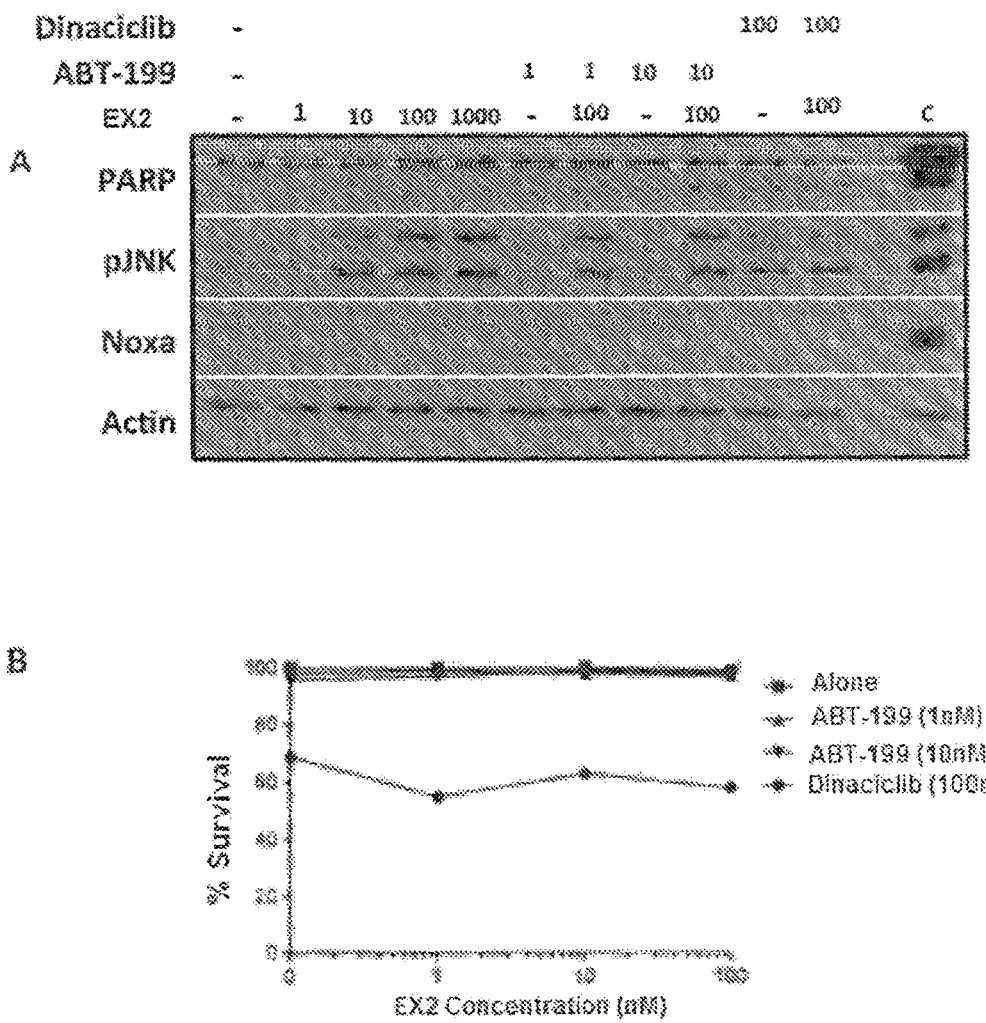
FIG. 8: Compounds of Formula (I) show no toxicity to normal peripheral lymphocytes and does not sensitize the cells to ABT-199. A) Western blots of cells from a healthy volunteer were incubated for 6 h with 0-1 μM compounds of Formula (I) alone or with 1-10 nM ABT-199, or 100 nM dinaciclib. "C"=a control cell line incubated with 2 μM vinblastine as a positive control for protein expression. B) survival curve of the same cells was measured by chromatin condensation assay with Hoechst stain.
Figure 9:
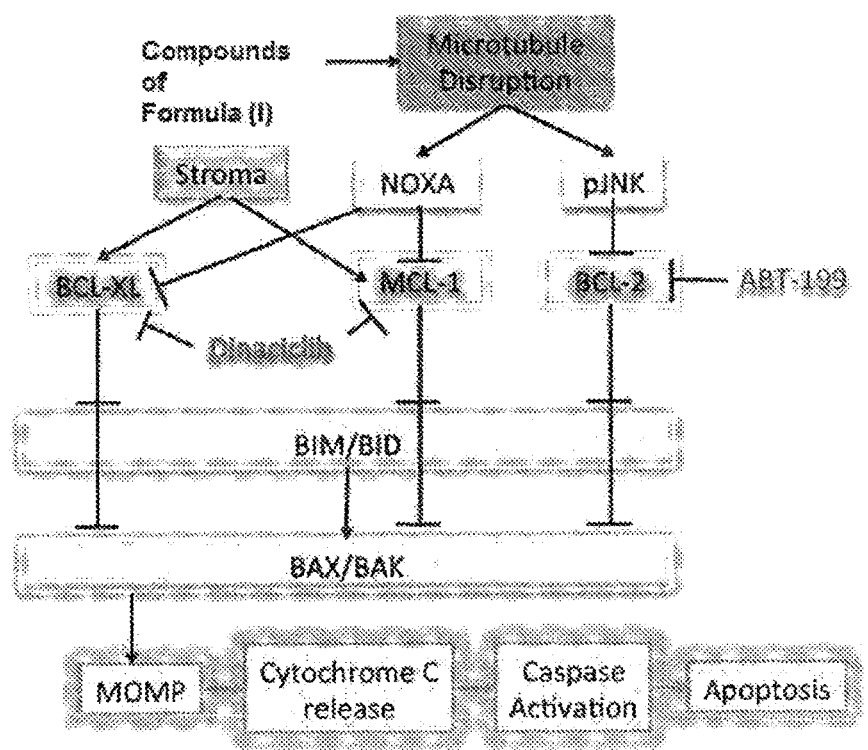
FIG. 9: Possible mechanism of action of compounds of Formula (I) leading to apoptosis. Compounds of Formula (I) bind to the colchicine site in microtubules, disrupting dynamic stability and resulting in tubulin depolymerization. As a result, JNK is phosphorylated and Noxa is induced. pJNK can activate a phosphorylation cascade causing inhibition of BCL-2. Noxa binds to MCL-1 targeting it for degradation. Transcription inhibition by the CDK inhibitor dinaciclib results in a rapid decrease in levels of MCL-1. Pro-apoptotic activators (e.g., BIM, BID) and effectors (e.g., BAX, BAK) interact leading to apoptosis. Co-culture with stromal cells causes protection through upregulation of BCL-XL and MCL-1 (and potentially BFL1, not shown). The BH3 mimetic ABT-199 inhibits only BCL-2 and will kill peripheral CLL cells, but not those on stroma. An agent that induces Noxa (e.g. compounds of Formula (I)) or inhibits MCL1/BCL-X expression (dinaciclib) can sensitize cells to ABT-199.
Figure 10:
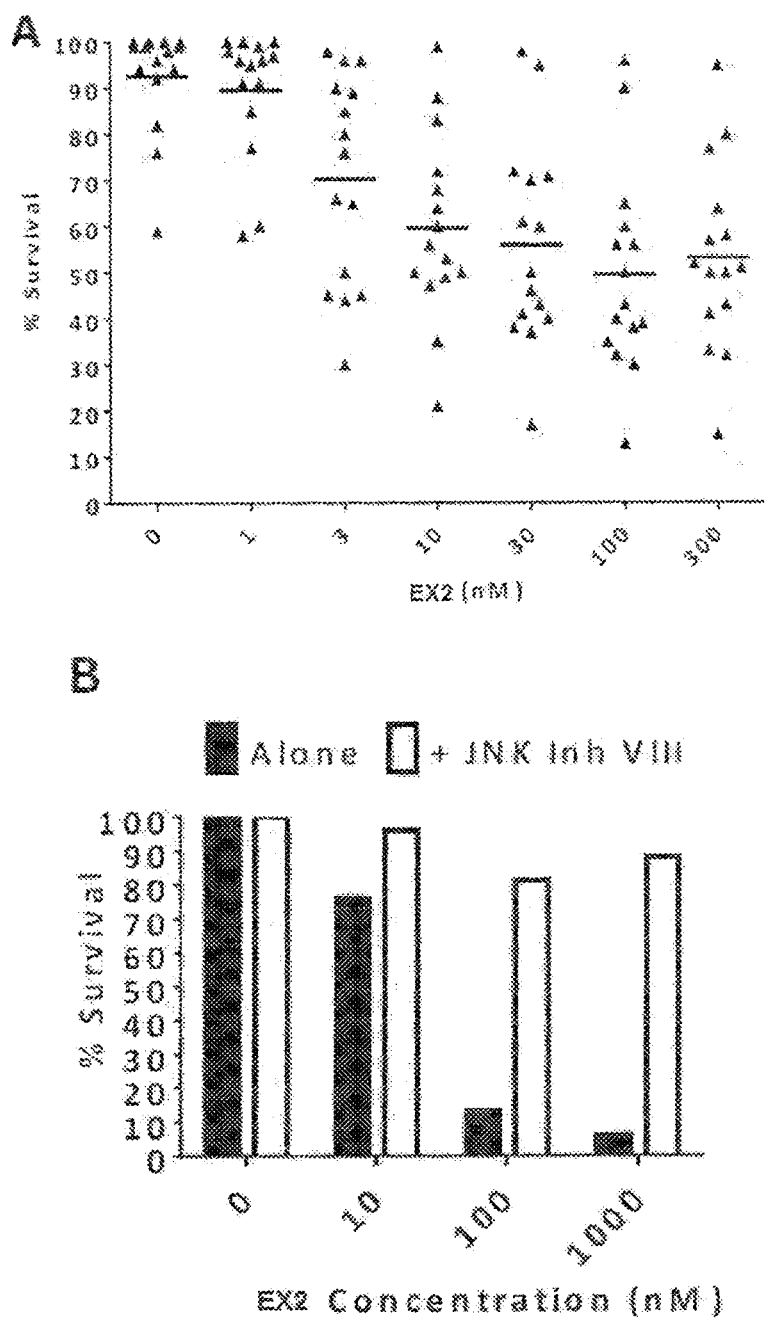
FIG. 10: Compounds of Formula (I) induce JNK-dependant apoptosis in CLL cells ex vivo. Freshly isolated CLL cells were incubated for 6 h ex vivo with EX2 alone or in the presence of JNK Inhibitor VIII. (A) represents the sensitivity of each individual patient sample to EX2 alone. (B) summarizes the results when the same samples were incubated with EX2 with or without the JNK Inhibitor VIIII (n=15).

To test the potential toxicity of EX2, normal peripheral lymphocytes were isolated from a healthy volunteer and incubated with EX2 alone or in combination with ABT-199. There was no significant PARP cleavage or chromatin condensation induced by EX2, although pJNK was activated; however, no Noxa was induced (FIG. 8). ABT-199 appeared to induce slight PARP cleavage but this was not increased by EX2, and no chromatin condensation was observed. This figure also shows the impact of combining EX2 with the CDK9 inhibitor dinacilib, which functions in this model primarily by preventing expression of MCL-1. Dinaciclib alone induced some apoptosis in normal leukocytes but this was not increased by EX2.

Figure 11:
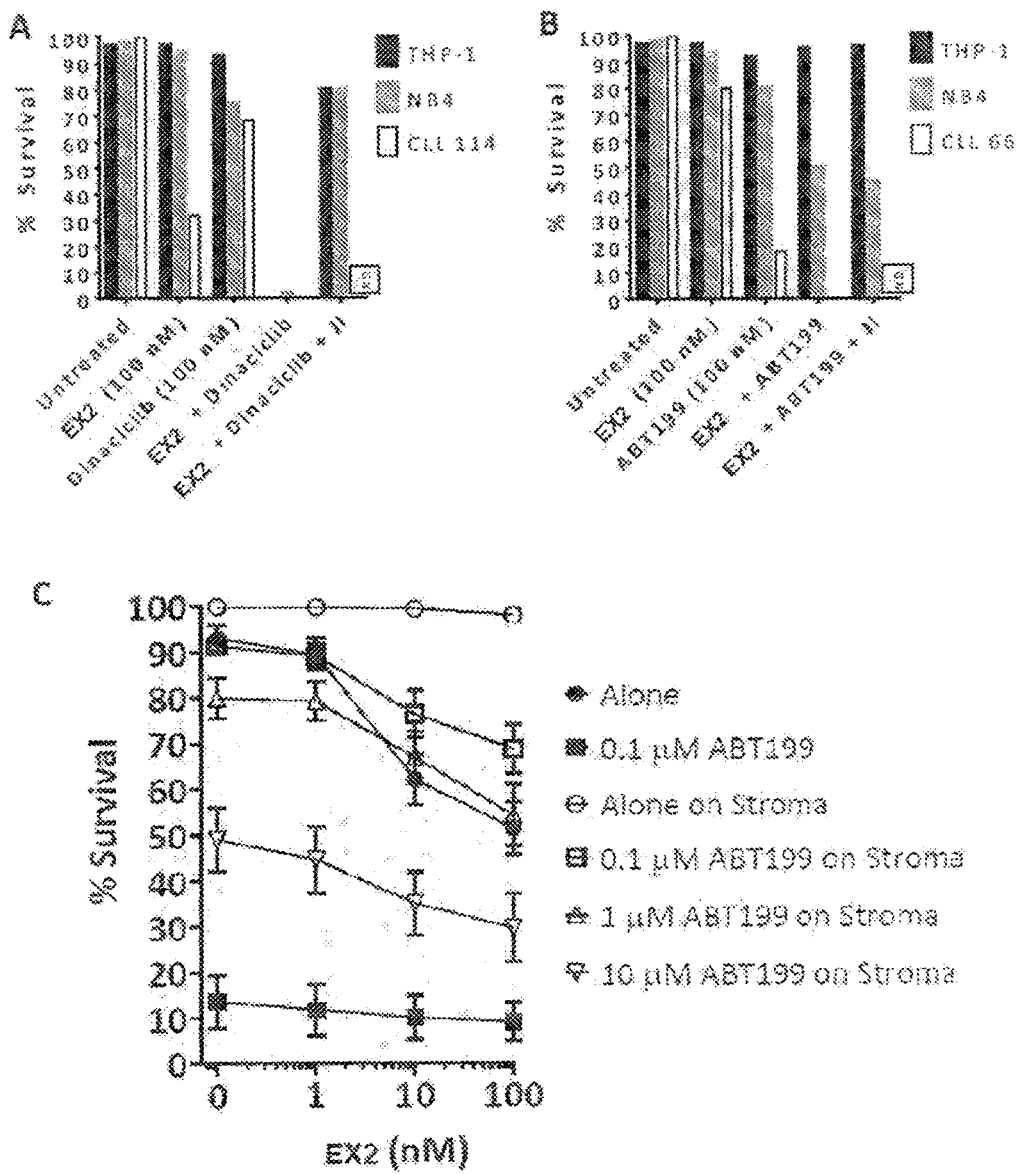
FIG. 11: Compounds of Formula (I) enhance apoptosis induced by ABT-199 or dinaciclib. Leukemia cell lines or CLL cells were incubated with EX2 dinaciclib (A) or ABT-199 (B) for 6 h. Consistent with previous vinblastine results, dinaciclib-mediated apoptosis requires JNK but ABT-199-mediated apoptosis does not. (C) Freshly isolated CLL cells were incubated alone and treated immediately, or plated on top of a monolayer of CD40L expressing L4.5 stroma cells for 24 h, then treated for 6 h with EX2±ABT-199 (n=16).

FIG. 11 shows Leukemia cell lines or CLL cells were incubated with EX2 dinacichb (A) or ABT-199 (B) for 6 h. Consistent with previous vinblastine results, dinaciclib-mediated apoptosis requires JNK but ABT-199-mediated apoptosis does not. (C) Freshly isolated CLL cells were incubated alone and treated immediately, or plated on top of a monolayer of CD40L expressing L4.5 stroma cells for 24 h, then treated for 6 h with EX2 ABT-199 (n=16).

Example 3

Phase 1b of Ibrutinib and Example 2 in Patients with Relapsed or Refractory CLL.

A phase 1 b trial is conducted. Table 1 provides a summary of the trial conditions. A list of abbreviations used in this Example is provided at the end of the Example. Example 2 is an example of a compound of Formula (I). The study is also capable of variation such a providing the patient first with ibrutinib followed by exposure to Example 2. Such a variation is to be taken into account during the following discussion of this one, non-limiting, embodiment.

TABLE 1

Summary of trial

| | |
|---|---|
| Title | A Phase Ib Study of Example 2 and Ibrutinib in Patients with Relapsed/ Refractory Chronic Lymphocytic Leukemia |
| Short Title | EXAMPLE 2 and ibrutinib in CLL |
| Phase | Ib |
| Methodology | Interventional study |
| Study Duration | 24 months |
| Objectives | To study the safety and efficacy of EXAMPLE 2 in combination with ibrutinib in patients with CLL |
| Number of Subjects | Up to 27 patients |
| Diagnosis and Main Inclusion Criteria | Patients with CLL |
| Study Product, Dose, Route, Regimen | Study product - Example 2, route - intravenous; dose level 1: 8 mg/m$^2$ on days 1 and 8 (cycle 1) followed by Example 2 on days 8 and 15 in combination with ibrutinib 420 mg daily beginning with cycle 2; cycle length is 21 days |
| Duration of administration | 6 cycles |
| Statistical Methodology | An open label, dose escalation prospective drug combination study |

Table 2 provides the study schema.

TABLE 2

Study schema

| Cycle | Example 2 | Ibrutinib |
|---|---|---|
| 1 | START 8 mg/m$^2$ IV on days 1, 8 (dose level 1)<br>12 mg/m$^2$ on days 1, 8 (dose level 2)<br>16 mg/m$^2$ on days 1, 8 (dose level 3)<br>4 mg/m$^2$ on days 1, 8 (dose level −1)<br>2 mg/m$^2$ on days 1, 8 (dose level −2)<br>See the decision tree below for dose modification in subsequent patients | — |
| 2-6 | 2-16 mg/m$^2$ IV on days 8, 15 (Dose corresponds to cycle 1 dose level in absence of DLT's) | 420 mg PO on days 1-21 |

Figure 12:
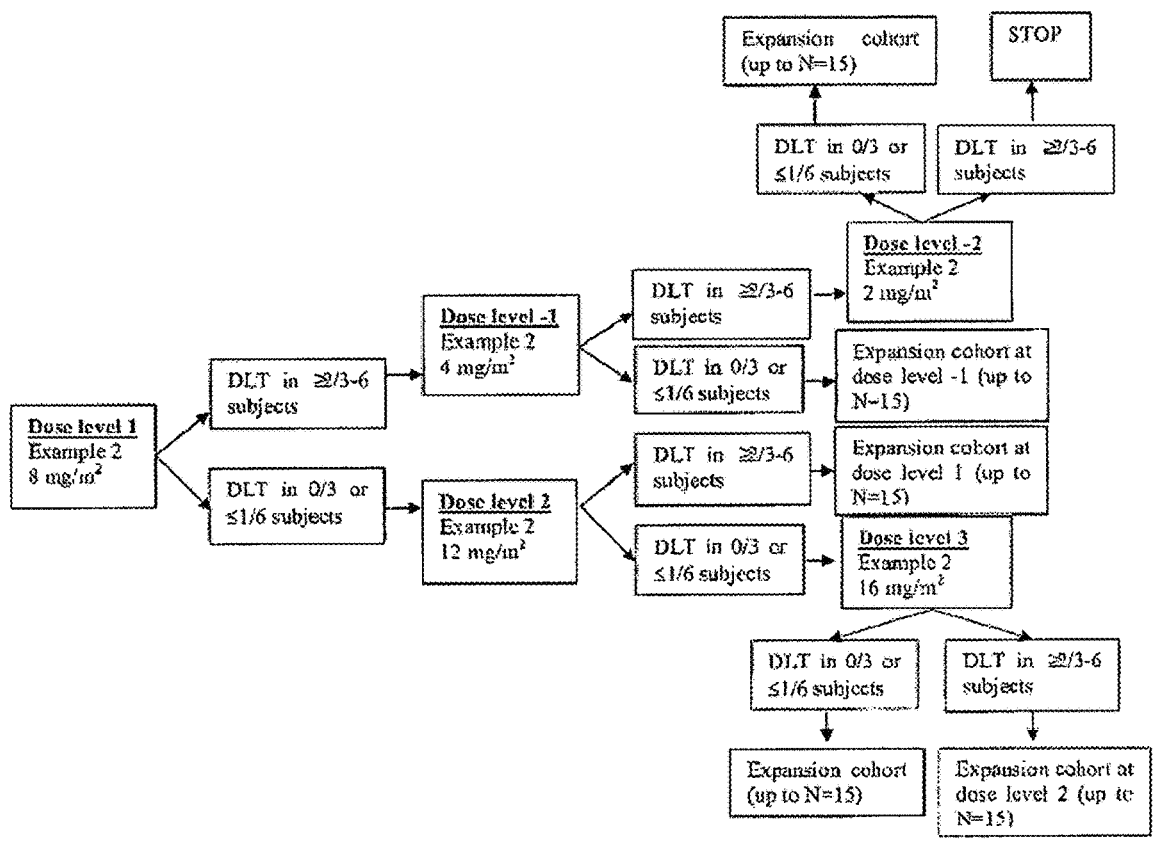
FIG. 12: Decision tree based on DLT's with cycles 1-2.

Decision Tree Based on DLT's with Cycles 1-2 is Shown in FIG. 12.

Study Design and Objectives

Study Design

This is a non-randomized open label Phase Ib dose escalation/finding study of EXAMPLE 2 in combination with ibrutinib in patients with relapsed/refractory CLL.

The study follows a standard 3+3 Phase I design. Once the maximum tolerated dose (MTD) is determined, an expansion cohort is enrolled. Dose limiting toxicities (DLT) are assessed during treatment cycles 1 and 2 to determine the MTD.

Patients with relapsed/refractory CLL who have not previously received ibrutinib or an alternative Bruton tyrosine kinase (BTK) inhibitor are accrued into this study. Patients who previously received drugs which inhibit kinases within the B-cell receptor (BCR) signaling cascade other than BTK (e.g. idelalisib, a PI3K inhibitor) are eligible. At dose level 1, patients receive Example 2 8 mg/m$^2$ in combination with ibrutinib (420 mg beginning with cycle 2). If safe, the dose of Example 2 is escalated to 12 and 16 mg/m$^2$ (dose levels 2 and 3). By contrast, dose de-escalation of Example 2 to 4 and 2 mg/m$^2$ (dose levels −1 and −2) occurs if DLT's are encountered. Once an MTD is determined an expansion cohort is accrued at that dose level of the combination to allow assessment of DLT's during subsequent cycles.

Accrual occurs simultaneously (see Table 2) and takes place at an ambulatory clinic under medical supervision.

Study Objectives
Primary:
  to establish an MTD of Example 2 in combination with ibrutinib, a BTK inhibitor, in patients with CLL
Secondary:
  to determine efficacy of Example 2 in combination with ibrutinib in patients with CLL
Tertiary/Exploratory Objectives:
  to explore the pharmacodynamic effects of Example 2 in CLL B-cells
  to assess whether established biomarkers (chromosomal abnormalities, immunoglobulin heavy chain [IGHV] mutational status, ZAP-70 and CD38 expression; p53 mutational status) predict response to EXAMPLE 2 in combination with ibrutinib in patients with relapsed/refractory CLL.
Study Endpoints
Primary
The primary study endpoint is based on toxicity.
Secondary
1) Efficacy. Patients who complete at least three 21-day cycles of study therapy (one cycle of EXAMPLE 2 alone and two cycles in combination with ibrutinib) are evaluable for response.
  a) Overall response rate is be determined based on the proportion of study participants who achieve CR, CRi, PR or nPR assessed two months after completion of therapy, as per IWCLL 2008 criteria (Hall& et al. (2008) *BLOOD:* 111: 5446-5456).
  b) Event-free survival (EFS), defined as the interval between the date of first study treatment and the date of objective signs of disease recurrence, subsequent anti-leukemic therapy, or death, whichever is first reported.
2) Observe the number of patients and number of cycles of treatment completed.
3) Biomarkers—to identify patient populations that are more or less likely to respond to the study regimen through the evaluation of biomarker analyses.
Rationale for Dose Selection The recommended Phase 2 dose (RP2D) of Example 2 is evaluated in subjects with advanced solid tumors. Dosing is at a level of 2.1 mg/m$^2$. The dose of 16 mg/m$^2$ is deemed to be an MTD. In this study, adverse events are seen across all dose groups. The two most common categories of AE's are gastrointestinal disorders (nausea, vomiting, constipation) and general disorders (predominantly fatigue). Disorders related to bone marrow suppression are rare. Anemia is reported in one patient at a dose level of 8.4 mg/m$^2$ and in two patients at a dose level of 18.9 mg/m$^2$. Two grade 4 events (myocardial infarction and peripheral neuropathy) occurred in the same subject at a dose level 18.9 mg/m$^2$.

Similarly, in a phase 11 study of Example 2 in patients with malignant pleural mesothelioma grade 1-2 gastrointestinal and general disorders are the predominant AE's: in 87% and 50% of patients correspondingly. Grade 3 fatigue is observed in 8% of patients. Finally, grade 1-2 anemia is reported in 33% of study participants.

The following considerations are taken into account when the combination therapy is being investigated in CLL.

First, the median age of patients with CLL at diagnosis is 72 years. Patients with CLL present with a median of 2 comorbidities at diagnosis and 46% carry at least one major comorbidity Thurmes et al. (2008) *Leuk Lymphoma* 49:49-56.

Second, bone marrow involvement and cytopenias are ubiquitous in CLL. Hence patients with CLL may experience an increased frequency of grade 3-4 hematologic toxicities with treatment as compared with patients with solid tumors who have intact bone marrow.

Third, since tumor cells accumulate in the peripheral blood where they may be particularly susceptible to cytotoxic agents, tumor lysis syndrome (TLS) is a concern in CLL. Since Example 2 induces rapid apoptosis of CLL cell in vitro it is wise to test lower doses of the drug than the currently proposed MTD, particularly in a setting where ibrutinib may provoke lymphocytosis. If rapid response occurs at lower doses of Example 2 than the previously established MTD, RP2D is revised down for patients with CLL ultimately reducing the risk of AE's.

Fourth, importantly for this study, Example 2 is shown to briefly disrupt microtubules in PBMCs at doses of 12.6 and 16 mg/m$^2$ suggesting that sufficient plasma concentrations can be achieved that induce the anticipated pro-apoptotic biomarkers (P-JNK and NOXA).

Thus, this study employs 8 mg/m$^2$ iv on days 1 and 8 (cycle 1) or 8 and 15 (cycles 2-6) of a 21-day cycle as a starting dose of Example 2. This dose corresponds to a dose one tier below that sufficient to induce disruption of microtubules, yet also is lower than the currently established MTD in a Phase I study of Example 2 in patients with solid tumors. Patients receive Example 2 for one 21-day cycle and receive ibrutinib at an FDA-approved dose (420 mg po daily) beginning with cycle 2. The study follows a standard 3+3 Phase I design (between 3 and 6 patients are enrolled at each dose tier). The dose of the drug is escalated to 16 mg/m$^2$, toxicities permitting. If toxicities emerge at dose level 1, the dose of Example 2 is de-escalated to 4 mg/m$^2$. Ibrutinib starting dose remains the same at every dose tier (420 mg), but is adjusted depending on toxicities. Preliminary assessment of response and pharmacodynamic endpoints of treatment with Example 2 is assessed at several dose levels allowing for more careful selection of RP2D in CLL.

Selection of Participants
  Eligibility Criteria
1. Patients have histologically or flow cytometry confirmed diagnosis of B-cell chronic lymphocytic leukemia/small lymphocytic lymphoma (B-CLL/SLL) according to NCI-WG 1996 guidelines Cheson et al. (1996) *Blood,* 87:4990-4997. The malignant B cells must co-express CD5 with CD19 or CD20. Patients who lack CD23 expression on their leukemia cells are examined for (and found not to have) either t(11;14) or cyclin D1 overexpression, to rule out mantle cell lymphoma.
2. Active disease meeting at least 1 of the IWCLL 2008 criteria for requiring treatment (Hallek et al. (2008) Supra):
  (1) A minimum of any one of the following constitutional symptoms:

(a) Unintentional weight loss >10% within the previous 6 months prior to screening.

(b) Extreme fatigue (unable to work or perform usual activities).

(c) Fevers of greater than 100.5 F for ≥2 weeks without evidence of infection.

(d) Night sweats without evidence of infection.

(2) Evidence of progressive marrow failure as manifested by the development of, or worsening of anemia or thrombocytopenia.

(3) Massive (i.e., >6 cm below the left costal margin), progressive or symptomatic splenomegaly.

(4) Massive nodes or clusters (i.e., >10 cm in longest diameter) or progressive lymphadenopathy.

(5) Progressive lymphocytosis with an increase of >50% over a 2-month period, or an anticipated doubling time of less than 6 months.

(6) Autoimmune anemia or thrombocytopenia that is poorly responsive to corticosteroids.

3. Patients must have received at least one prior therapy for CLL.

4. Patients must have ECOG performance status ≤2.

5. Patients must have organ function as defined below:
  direct bilirubin ≤2×institutional ULN (unless due to known Gilbert's syndrome or compensated hemolysis directly attributable to CLL)
  AST or ALT less than 2.5× institutional ULN
  estimated CrCL using the Cockroft-Gault equation ≥50 mL/min.
  platelets ≥50,000/mm$^3$ independent of transfusion support with no active bleeding.

6. Women of childbearing potential must have a negative serum β-human chorionic gonadotropin or urine pregnancy test at screening.

7. All patients of reproductive potential (heterosexually active men and women) must agree to a use of a barrier method of contraception and a second method of contraception and men must agree not to donate sperm during the study and for 4 weeks after receiving the last dose of study treatment.

Exclusion Criteria

1. Prior therapeutic intervention with any of the following:
  a) ibrutinib or another inhibitor of Bruton tyrosine kinase at any time;
  b) nitrosoureas or mitomycin C within 6 weeks;
  c) therapeutic anticancer antibodies (including rituximab) within 4 weeks;
  d) radio- or toxin-immunoconjugates within 10 weeks;
  e) all other chemotherapy, radiation therapy within 3 weeks prior to initiation of therapy.

2. Inadequate recovery from adverse events related to prior therapy to grade 9 (excluding Grade 2 alopecia and neuropathy).

3. Chronic use of corticosteroids in excess of prednisone 20 mg/day or its equivalent. Stem cell transplant recipients must have no evidence of active graft-versus-host disease.

4. Use of full dose, therapeutic anti-coagulation with warfarin, unfractionated or low molecular weight heparins or other anticoagulants (e.g., direct thrombin inhibitors—dabigatran or anti-Xa agents—rivaroxabanlapixiban). Low dose warfarin for catheter prophylaxis or aspirin ≤325 mg/day is acceptable 5. Concomitant use of strong CYP inducers or inhibitors including nutraceutical preparations, e.g., St John's Wort 6. History of prior malignancy except:
  a) Malignancy treated with curative intent and no known active disease present for years prior to initiation of therapy on current study;
  b) adequately treated non-melanoma skin cancer or lentigo maligna without evidence of disease;
  c) adequately treated in situ carcinomas (e.g., cervical, esophageal, etc.) without evidence of disease;
  d) asymptomatic prostate cancer managed with "watch and wait" strategy;
  e) myelodysplastic syndrome which is clinically well controlled and no evidence of the cytogenetic abnormalities characteristic of myelodysplasia on the bone marrow at screening.

7. Uncontrolled immune hemolysis or thrombocytopenia (positive direct antiglobulin test in absence of hemolysis is not an exclusion).

8. Thrombotic events (pulmonary embolism; deep venous thrombosis) within 6 month prior to start of therapy 9. Human Immunodeficiency Virus (HIV) antibody positivity or active hepatitis B or C. Intravenous immunoglobulin (IVIG) can cause a false positive hepatitis B serology. If patients receiving routine IVIG have core antibody or surface antigen positivity without evidence of active viremia (negative hepatitis B DNA) they may still participate in the study, but should have hepatitis serologies and hepatitis B DNA monitored periodically by the treating physician.

10. Class III or Class IV New York Heart Association Congestive Heart Failure or acute coronary syndrome within 8 weeks prior to C1D1.

11. Major surgery (requiring general anesthesia) within 30 days prior to initiation of therapy.

12. Inability to swallow and retain an oral medication. Patients with clinically significant medical condition of malabsorption, inflammatory bowel disease, chronic conditions which manifest with diarrhea, refractory nausea, vomiting or any other condition that interferes significantly with the absorption of study drugs are excluded.

13. Any condition for which participation in the study is judged by the Investigator to be detrimental to the patient with inter-current illness including, but not limited to an uncontrolled active infection; unstable angina pectoris; uncontrolled cardiac arrhythmia or psychiatric/social situations that would jeopardize compliance with study requirements.

Treatment Plan

Treatment is administered on either inpatient or outpatient basis. Expected toxicities and potential risks as well as dose modifications for Example 2 and ibrutinib are described below (Expected Toxicities and Dosing Delays/Modifications). No investigational or commercial agents or therapies other than those described below are administered with the intent to treat the participant's CLL/SLL.

Study Procedures

The study consists of a Pre-treatment Period with baseline tumor assessment before Example 2 administration, a Treatment Period with up to six 21-day cycles and a Post-treatment Period (end-of-treatment visit and post-treatment follow-up visits). Patients receive a total of six cycles of therapy unless treatment is discontinued for one of the pre-specified reasons.

The timing of study assessments and procedures is presented by study cycle and day and are abbreviated by the following references: Cycle (C) and Day (D) number, as in C1D1 (Cycle 1 Day 1). C1 D1 is the date of first dose of Example 2. Cycles and days within each week are numbered sequentially thereafter.

Pretreatment Period

During the Pretreatment Period, patients are screened and consented for the study. Evaluations performed as part of routine care before informed consent are utilized as screening evaluations if done within the defined time period.

Patients undergo screening evaluations to determine study eligibility, including medical history, physical examination, hematology and biochemical/metabolic laboratory profiles, urinalysis, coagulation, pregnancy test, and all qualifying disease assessments. All qualifying screening and eligibility assessments are performed within 30 days before the first dose of study treatment. Tests used for baseline disease assessments are performed within specified time frame of the initial dose of study treatment (CT scans—30 days, genetic markers [cytogenetics and FISH], CD38 and bone marrow biopsy—6 months, HIV and hepatitis testing—12 months, ZAP-70—at any time since diagnosis and IGI-JV mutational status—at any time since diagnosis, if available).

Treatment Period

A cycle is defined as every 21 days. Example 2 is administered at the doses detailed below for up to 6 cycles, and in combination with ibrutinib in cycles 2 through 6. Clinic visits are performed every cycle on Day 1. Under certain circumstances Day 1 may be delayed by not more than 3 days or occur earlier than scheduled by not more than 1 day during cycles 2-6.

Assessment of adverse events occur on Days 1, 2, 8 and 15 of cycle 1; Days 1, 8, 9 and 15 of cycle 2; and Days 1, 8 and 15 of subsequent cycles.

Clinical laboratory assessments are collected on D1 of each cycle visit, or ≤48 hours before those visits, and the test results are available and reviewed before the first dose of Example 2 (C1D1) or ibrutinib (C2-6). Screening assessment tests are considered as C1D1 tests if performed ≤72 hours before the first dose of study treatment; otherwise, the required evaluations are repeated within this timeframe. Additional clinical laboratory assessments are collected on C1D1, C1D2; as well as C1D8, C1D15, C2D8, C2D9 and C2D15.

On C1D1 and C2D8 all qualifying patients provide samples for biomarker analysis.

Patients also undergo CT staging on C4D1 (or ≤72 hours before C4D1 visit) to assess for disease progression. If it is suspected that disease progression has occurred prior to beginning of C4, CT scanning may be performed during C1-3.

The study treatment period ends on day 21 of the last cycle of study treatment. Patients return to the study site 2 months (±7 days) after the last 21-day cycle of study treatment for an end of treatment visit. Laboratory and physical examinations as well as an ECG are performed. Radiographic assessment is performed 2 months (±7 days) after the last 21-day cycle. If a complete response is suspected, a bone marrow biopsy is performed no later than 3 months after the last 21-day cycle of study treatment. Adverse events that are related to study treatment and are ongoing at the time of this visit are followed until resolution or until considered irreversible by the Lead P1.

Post Treatment Period

Disease assessments are obtained in the post treatment period, following the original schedule or earlier, if clinically indicated. Specifically, evaluations are performed 3, 6, 9 and 12 months after the end-of treatment visit, followed by every 4-6 months thereafter and include laboratory assessments and physical examination at every visit. CT scans are obtained at 6 and 12 months after the end-of-treatment visit (±7 days) and as clinically indicated thereafter. Such evaluations are performed regardless of whether patients choose to continue ibrutinib treatment or not. Patients who continue ibrutinib therapy participate in EFS analysis.

Treatment

Formulation, Storage and Handling of Example 2

Example 2 is obtained from Bionomics Ltd, Australia. The investigational product is 'Example 2 Solution For Injection', which is a sterile solution of Example 2 manufactured under current Good Manufacturing Practices (cGMP) and which contains 10 mg/mL of the phosphate prodrug equivalent (un-ionized) dissolved in saline. The investigational product is a clear, colorless to yellow liquid presented in a clear glass vial and is intended to be diluted with commercially available sterile 0.9% saline prior to iv administration. Dilution of the investigational product for use in clinical trials is performed using aseptic techniques. The 10 mg/mL Example 2 Solution For Injection drug product is intended to be stored and shipped frozen in order to maximize the shelf-life and quality of the drug. The diluted study drug is stored at controlled room temperature or lower (refrigerated) and can be kept for up to 28 hours before use. Protection from light is not necessary. Example 2 Solution For Injection has been shown to be compatible with commercially available saline iv administration bags and a range of infusion set components. Stability trials of Example 2 drug product stored at −20° C. have shown acceptable product recovery and purity up to 48 months.

The investigational product is diluted, when required, with commercially available sterile 0.9% w/v saline using aseptic techniques. Time is allocated to thaw the investigational product to ambient temperature prior to any dilution with saline. It is recommended that the dilution of the investigational product with 0.9% w/v saline be performed on the day prior to dosing.

Formulation, Storage and Handling of Ibrutinib

Ibrutinib is obtained from commercial supply and used according to manufacturers instructions.

Treatment Description

Treatment is summarized in Table 3.

TABLE 3

Treatment description

| Agent | Pre-medications; Precautions | Dose | Route | Schedule | Cycle Length |
|---|---|---|---|---|---|
| Example 2 | None | According to dose level - see below | iv over 10 min | Days 1 and 8 (C1); Days 8 and 15 (C2-6) | 21 days (3 weeks) |
| Ibrutinib* | None | 420 mg as per package insert | PO | Daily beginning with C2D1 | |

*Ibrutinib is self-administered by the study participants.

Overall Study Design

This is an open-label, Phase Ib trial with a dose escalation phase, followed by a MTD dose expansion phase. The primary objective of the dose escalation phase is to evaluate the MTD of Example 2 in combination with ibrutinib in patients with relapsed/refractory CLL. The MTD dose expansion phase further evaluates the safety and efficacy of the combination in up to 15 patients at the MTD level.

Dose Escalation Phase

Up to three dose levels are evaluated in the 'dose escalation' phase.

The dose levels of Example 2 are 8 mg/m² (Dose Level 1), 12 mg/m² (Dose Level 2) and 16 mg/m² (Dose Level 3) IV on days 1 and 8 of cycle 1 and days 8 and 15 of cycles 2-6 (Table 4).

If DLTs are observed at dose level 1 (as described below), the dose of Example 2 is de-escalated to 4 mg/m² (Dose Level −1). If DLTs are observed at dose level −1 (as described below), the dose of Example 2 is de-escalated to 2 mg/m² (Dose Level −2).

Starting dose of Example 2 is 8 mg/m² IV on days 1 and 8 of cycle 1, when BCN105P is administered as a single agent prior to initiation of ibrutinib. Beginning with cycle 2, ibrutinib is administered concomitantly with Example 2 at a starting dose of 420 mg PO daily. To allow ibrutinib-mediated egress of CLL cells from the lymph nodes niche, Example 2 is administered on days 8 and 15 during cycles 2-6. The starting dose of ibrutinib remains unchanged at each dose level.

Each cycle lasts for 21 days. Provided no toxicities occur, each patient is treated for 6 cycles.

The 'dose escalation' phase of the study follows a standard 3+3 Phase I design. At a given dose level, 3 patients are enrolled. If all 3 patients complete the first cycle of therapy without any dose-limiting toxicities (DLTs), the next cohort of 3 patients is enrolled at the next higher dose level. If ⅓ patients develops a DLT the cohort are expanded to 6 patients. However, if either ≥⅔ or ≥2/6 patients in any dose tier have DLTs, the previous dose tier is defined as the maximum tolerated dose (MTD) of the combination. Once the MTD is determined, an expansion cohort is accrued to a total of 15 patients at that dose level, i.e. 12 or 9 additional patients are accrued.

TABLE 4

Dose levels planned for dose escalation phase of the study

| Dose Level | Example 2 (Cycles 1-6) intravenously on days 1 and 8 of cycle 1 and days 8 and 15 of cycles 2-6 Each cycle is 21 days | Ibrutinib (Cycles 2-6) po daily on days 1-21 of 21-day cycles |
|---|---|---|
| −2 | 2 mg/m² | 420 mg |
| −1 | 4 mg/m² | 420 mg |
| 1 | 8 mg/m² | 420 mg |
| 2 | 12 mg/m² | 420 mg |
| 3 | 16 mg/m² | 420 mg |

*Dose Level −1 is studied only if more than one patient develops a DLT in Dose Level 1

For all the Dose Levels in the dose-escalation phase, should more than one patient develop a DLT in the respective Dose Level; the dose of Example 2 is reduced according to the plan shown in Table 4.

If no significant toxicities are observed, the dose escalation part of the study is anticipated to enroll between 9 and 18 patients. Treatment continues for either a) 6 cycles; or b) until disease progression or unacceptable toxicities, if they occur prior to completion of 6 cycles of therapy.

Dose Extension Phase

In the 'dose extension' phase patients are treated at the MTD of Example 2 in combination with ibrutinib, determined in the dose escalation phase. Treatment continues for either a) 6 cycles; or b) until disease progression or unacceptable toxicities, if they occur prior to completion of 6 cycles of therapy. In this phase, patients are assessed for safety (CTCAE v.4.03) and efficacy parameters (overall response rate [ORR] and progression free survival [PFS]).

Patients Who Either:
a) fail to complete the first efficacy evaluation (scheduled at the beginning of C4) for any reason or
b) receive <2 doses of Example 2 during each of the first 3 cycles or <14 of 21 doses of ibrutinib during each of cycles 2 and 3 are not considered for efficacy evaluations, unless disease progression has occurred prior to the first scheduled efficacy evaluation.

Pre-Treatment Criteria
C1 D1
Hematologic parameters: platelets must be >50,000/mm³ (in absence of transfusion support); hemoglobin >8 g/dL (transfusion support permissible);
Non-hematologic parameters: direct bilirubin ≤2× institutional ULN (unless due to known Gilbert's syndrome or hemolysis directly attributable to CLL); AST or ALT<2.5× institutional ULN.

Vital signs, all laboratory data (including pregnancy testing) are reviewed by the treating physician prior to administering the first dose of a study agent.

Subsequent Cycles
Hematologic parameters: platelets must be >50,000/mm³ or >75% of baseline, whichever is lower (without transfusion support); hemoglobin >8 g/dL (transfusion support permissible); ANC>1000/mm³ or >75% of baseline, whichever is lower (G-CSF support permissible at the discretion of the investigator in case of ANC<1000)
Non-hematologic parameters: direct bilirubin ≤2× institutional ULN (unless due to known Gilbert's syndrome or hemolysis directly attributable to CLL); AST or ALT<2.5× institutional ULN.

Administration of Example 2

The starting dose of Example 2 for all patients is 8 mg/m² infused IV over 10 minutes on Days 1 and 8 of a 21-day cycle with cycle 1; on Days 8 and 15 of a 21-day cycle beginning with cycle 2 for a maximum of 6 cycles. The dose of Example 2 is calculated based on the actual body weight using Mosteller or DuBois formulas for BSA.

The choice of a formula is based on the institutional guidelines.

Mosteller formula: BSA=SQRT ([Height (cm)×Weight (kg)]/3600),

DuBois formula: BSA $(m^2)=0.20247 \times \text{Height}(m)^{0.725} \times \text{Weight}(kg)^{0.425}$.

The dose is recalculated with each cycle according to the same formula used with previous cycle.

Recommended duration of the infusion: 10 minutes; observation period following infusion: 15 minutes.

Administration of Ibrutinib

Ibrutinib is self-administered beginning with C2D1. Ibrutinib is taken orally, with 8 ounces (approximately 240 mL) of water. The capsules are swallowed intact, not less than 30 minutes before or 2 hours after a meal. Doses are taken in the morning at about the same time each day. If the patient misses a dose, it can be taken as soon as possible on the same day with a return to the normal schedule the following day. The patient keeps a diary where he/she records the date and time that ibrutinib was taken.

On days when ibrutinib is administered with Example 2 (days 8 and 15 of cycles 2 through 6), ibrutinib is given in the clinic at least 30 minutes prior to administration of Example 2.

Duration of Therapy and Follow-Up for Individual Patients

Study participants receive up to 6 cycles of Example 2 and ibrutinib assuming no limiting toxicity occurs.

Expected Toxicities and Dosing Delays/Dose Modifications

Anticipated Toxicities: Example 2

Based on the data available for Example 2, the following is a list of effects that could be encountered in patients administered Example 2 via the iv route:
 Gastro-intestinal effects (nausea, vomiting, diarrhea or constipation).
 Hematological changes (myelosuppression, platelet counts, reticulocyte numbers, slight delays in coagulation)
 Drowsiness, fatigue
 Weakness in arms and legs
 General malaise
 Rib pain
 Increase in symptoms of infections/infestations (herpes simplex; oral candidiasis)
 Increased skin sensitivity
 Effects on sperm count
 Cardiovascular effects, myocardial infarction and transient blood pressure changes.
 Peripheral sensory neuropathy
 Elevation in the liver function tests
 non-ST segment elevation myocardial infarction
 Thromboembolic events (including pulmonary embolism, deep vein thrombosis)
 Stroke Although Example 2 showed no effects on the cardiovascular system when tested in dogs, potential effects on the cardiovascular system cannot be ruled out. Based on findings from the 2-cycle rat study for Example 2, dose-dependent, reversible cardiomyopathy was observed in rats. Signs of cardiomyopathy were decreased in severity and incidence by 14 days after the 2-cycles of treatment, indicating recovery or reversibility of the effects. The implications of these findings for humans are not clear as these cardiovascular effects were not observed in dog toxicity studies. Furthermore, in a cardiovascular safety pharmacology study in telemetered dogs, there were no effects on cardiovascular or respiratory function following doses up to 0.8 mg/kg (the highest dose assessed). Also, based on in vitro testing, the IC50 values for hERG channel inhibition for both Example 1 and Example 2 are much greater than 2.5 and 486.0 µg/mL, respectively, with the first dose representing what was maximally feasible in the test system, and the latter dose representing a level 30 times the highest free plasma concentration predicted to be present after administration of Example 2 at 100 times the theoretical starting dose in the clinic. Thus an effect on the hERG channel is expected to be slight, if any, at efficacious doses of Example 2.

Of the effects listed above, effects on sperm count, hematologic changes, and potential cardiovascular effects (myocardial infarctions; transient blood pressure changes) could be considered to be risks of potential severity and seriousness. It is worth noting that hematologic effects and effects on sperm count are not unexpected effects of drugs that inhibit tubulin polymerization and subsequent cell proliferation.

Efficacy

All subjects who completed two cycles of study treatment are evaluable for efficacy.

Disease Evaluations

Physical examination, which focuses on documenting a change in the number of site and size of lymphadenopathy, hepato- and splenomegaly, is done as part of the full disease evaluation during treatment and at months 3, 6, 9 and 12 after the end-of-study visit and every 4-6 months thereafter, until disease progression or death.

Complete blood count (CBC) with measurement of parameters including ALC are obtained on Days 1, 2, 8 and 15 of C1; Days 1, 8, 9 and 15 of C2; on day 1 for the remaining four cycles, every 3 months for the first 12 months, and every 4-6 months thereafter until disease progression or death.

Serum biochemistry/metabolic panel are obtained on D1 of each cycle; 3 and 6 hours after administration of Example 2 on C1D1 and C2D8; and on C1D2 and C2D9.

Computed tomography (CT) scan of neck, chest, abdomen and pelvis with intravenous contrast where possible are performed at screening, on C4D1 (or ≤72 hours prior), at the end of treatment visit (2 months±7 days after completion of the last 21-day cycle of treatment), at months 6 and 12 after the end of treatment visit (±7 days), and as clinically indicated thereafter. Site measurement is performed according to IWCLL 2008 criteria.

A unilateral bone marrow aspirate and biopsy is obtained during screening or up to 6 months before the first dose of study drug. Subjects who have bone marrow aspirate and biopsy results since completion of their last therapy for CLL may use those results if they were obtained within 6 months prior to the first dose of study drug. If the subject's physical examination findings, laboratory and radiographic evaluations suggest that CR has been obtained, a bone marrow aspirate/biopsy is obtained to confirm the CR within 30 days after the end-of-treatment visit.

Criteria for Response

Modified IWCLL guidelines Hallek et al. (2008) *Blood*, 111:5446-5456 are used to measure response in CLL/SLL patients.

Objective response for CLL/SLL patients is defined as CR, Cri, nPR and PR. Patients are assessed for response at the end of treatment. If there is a clinical suspicion for progression, disease assessment is performed at any time.

Complete remission (CR) requires all of the following:
1. Peripheral blood lymphocytes (evaluated by blood and differential count) below $4 \times 10^9$/L
2. Absence of significant lymphadenopathy (lymph nodes >1.5 cm in diameter) by physical examination and imaging, if baseline scans were abnormal
3. No hepatomegaly or splenomegaly by physical examination and imaging, if baseline scans were abnormal
4. Absence of constitutional symptoms (B symptoms)
5. Blood counts:
 Neutrophils $>1.5 \times 10^9$/L without need for exogenous growth factors
 Platelets $>100 \times 10^9$/L without need for exogenous growth factors
 Hemoglobin >11.0 g/dL without red blood cell transfusion or need for exogenous erythropoietin
6. Bone marrow aspirate and biopsy must have the following findings
 normocellular for age
 less than 30% of nucleated cells being lymphocytes
 no B-lymphoid nodules (confirmed by THC)

Complete response with incomplete marrow recovery (CRi): patients who fulfill all the criteria for a CR but who have a hypocellular marrow and persistent anemia or thrombocytopenia or neutropenia unrelated to CLL but secondary to drug toxicity. If the marrow is hypocellular, a repeat determination is performed after 4 weeks, or when peripheral blood counts have recovered.

Nodular partial response (nPR): patients who fulfill all the criteria for CR but who have bone marrow evidence of B-lymphoid nodules by IHC.

Partial Remission (PR) Requires:
1. Blood count should show one of the following results:
   Neutrophils more than $1.5 \times 10^9$/L without need for exogenous growth factors
   Platelet counts $>100 \times 10^9$/L or 50% improvement over baseline without need for exogenous growth factors
   Hemoglobin >11.0 g/dL or 50% improvement over baseline without requiring red blood cell transfusions or exogenous erythropoietin
And two of the following three criteria:
2. Decrease in number of blood lymphocytes by 50% or more from the value before therapy
3. Reduction in lymphadenopathy by physical examination or imaging as defined by:
   A decrease in lymph node size by 50% or more either in the sum products of up to 6 lymph nodes, or in the largest diameter of the enlarged lymph node(s) detected prior to therapy
   No increase in any lymph node, and no new enlarged lymph node
   In small lymph nodes (<2 cm), an increase of less than 25% is not considered to be significant
4. A reduction in splenomegaly and hepatomegaly by 50% or more, by physical examination or imaging.

PR with Lymphocytosis:
Since ibrutinib may induce persistent lymphocytosis, it should not interfere at the time of designation of a PR. PR with lymphocytosis should be based on other measurable aspects of disease other than ALC Cheson et al. (2012) *J Clin Oncol*, 30:2820-2822.

Correlative Studies

All study participants undergo peripheral blood collection before drug administration and 0.5, 3 and 6 hours after completion of the infusion of the 1st dose of Example 2 with cycle 1 (Example 1 alone), as well as with cycle 2 (C2D8—Example 2 in combination with ibrutinib). 15 mL of blood is collected at all time points (participant number, and date and time of collection are recorded). Venous blood samples are transported to Dr. Danilov/Eastman's laboratories within 1 hour after collection. CLL B-cells are isolated using Ficoll-Hypague gradient. An aliquot of cells are flash frozen immediately after purification for subsequent protein analysis.

The sample of CLL cells obtained prior to therapy is incubated with Example 2 ex vivo and analyzed for expression of P-JNK and NOXA similar to that presented in FIG. 14. This provides baseline data reflecting variability between patient samples, and thereby help to explain any potential variation observed in the samples analyzed following treatment.

The following pharmacodynamic endpoints and additional biomarkers are evaluated:

Protein analysis from all blood collections are assayed by immunobloting for JNK activation (phospho-JNK) and NOXA expression.

CLL cells are also analyzed by centrifugation for Example 1-mediated dissociation of tubulin.

The remaining CLL B-cells are viably frozen at −70° C. until further processing including RNA and DNA isolation.

A preliminary assessment is performed as to whether prognostic biomarkers (IGHV, ZAP-70 expression, CD38 expression and CLL FISH panel) are of value to predict response to Example 2/ibrutinib combination in CLL. Such biomarkers (with the exception of IGHV) are routinely obtained during the diagnostic work-up of CLL to delineate prognosis in an individual patient.

IGHV mutational status (if not available after routine testing) is assessed employing IgH Somatic Hypermutation Assay v.2.0 (InVivoSribe Technologies).

p53 mutational status (direct sequencing, at OHSU)

Statistical Considerations

This Phase Ib study is conducted using the '3+3' strategy: in the first stage, up to 6 patients are administered 8 mg/m$^2$ Example 2 in combination with ibrutinib (dose level 1). This is done in up to two steps. First, up to 3 patients receive the drug. If there is two or more toxicities there is no dose escalation. If there are no toxicities the dose is escalated in another cohort. If there is exactly one toxicity, up to 3 additional patients are administered the same dose. If there is no toxicities in this second cohort of 3 the dose is escalated in another cohort. If there is at least one more toxicity the dose is not escalated. In this second stage, if 2 (or more) experience toxicity, dose level 1 is considered MTD, following by an expansion cohort at that dose level. If 1 (or less) experience a toxicity at the second stage, then expansion cohorts are accrued at that dose level (up to 15 subjects).

If 2 (or more) experience toxicity at stage 1, an alternative second cohort of up to 6 subjects is administered 4 mg/m$^2$ Example 2. If the number of toxicities in this alternative second stage is 2 or more, a third cohort of up to 6 subjects is administered 2 mg/m$^2$ Example 2. If the number of toxicities in this cohort is 2 or more, Example 2/ibrutinib combination is rejected.

Table 5 below shows the probability of dose escalation as a function of the underlying toxicity frequency. For instance, if the true frequency of toxicity at a particular dose level is 10% there is a 91% chance that the dose is escalated. If the true frequency is 50% there is only a 17% chance it is escalated.

TABLE 5

Probability of dose escalation

| Underlying Toxicity Frequency (%) | Escalation Probability (%) |
|---|---|
| 10 | 91 |
| 20 | 71 |
| 30 | 49 |
| 40 | 31 |
| 50 | 17 |

The frequency of toxicities in the expansion cohorts (N=15) is reported along with 95% exact binomial confidence intervals. Table 6 below shows the expected limits of these intervals. For instance, if the true frequency of toxicities is 10%, the 95% confidence interval is expected to range from 1.6% to 34.8%

TABLE 6

Interval Limits

| Actual probability of toxicity, % | Expected Limits of 95% Exact Binomial, % | |
|---|---|---|
| 10 | 1.6 | 34.8 |
| 20 | 5.3 | 47.2 |
| 30 | 10.6 | 57.6 |
| 40 | 17.1 | 67.0 |
| 50 | 24.6 | 75.4 |

In a Phase II study of ibrutinib in relapsed/refractory CLL, an overall response rate (ORR) has been reported in 90% of patients (including PR with lymphocytosis), however CR was uncommon (Byrd et al. (2013) *N Engl J Med*, 369:32-42). The Example 2 and ibrutinib combination is considered efficacious and deemed for further evaluation if a CR rate>30% is achieved on an expansion cohort. The frequency of CR is reported along with 95% exact binomial confidence intervals (assuming that an expansion cohort enrolls ten patients, if a true CR is 30% the 95% confidence interval is expected to range from 8.1% to 63.9%). The distribution of EFS are reported using a Kaplan-Meier estimate with confidence intervals.

It is expected that the clinical Ib data will show synergy between ibrutinib and Example 2 in the treatment and management of CLL.

LIST OF ABBREVIATIONS

AE—adverse events
ALC—absolute lymphocyte count
ALT—alanine transaminase
ANC—absolute neutrophil count
aPTT—activated partial thromboplastin time
AST—aspartate aminotransferase
BCR—B-cell receptor
BTK—Bruton tyrosine kinase
CBC—complete blood count
CCRC—Clinical Cancer Review Committee
CIRS—Cumulative Illness Rating Scale
CLL—chronic lymphocytic leukemia
CPHS—Committee for the Protection of Human Subjects
CR—complete response
CrCL—(estimated) creatinine clearance
CRi—complete response with incomplete marrow recovery
CT—computed tomography
CTO—Clinical Trials Office
DHMC—Dartmouth-Hitchcock Medical Center
DLT—dose-limiting toxicity
DSMAC—Data Safety Monitoring and Accrual Committee
cCRF—electronic case report form
EFS—event-free survival
FISH—fluorescent in situ hybridization
IGHV—immunoglobulin heavy chain gene
IHC—immunohistochemistry
IRB—Institutional Review Board
IV—intravenously
IWCLL—International Workshop on Chronic Lymphocytic Leukemia
KCI—Knight Cancer Institute
LDH—lactate dehydrogenase
MTD—maximum tolerated dose
NCCC—Norris Cotton Cancer Center
nPR—nodular partial response
OHSU—Oregon Health and Science University
ORR—overall response rate
OS—overall survival
PFS—progression-free survival
PI—principal investigator
PI3K—phosphoinositide-3 kinase
PO—by mouth
PR—partial remission
SAE—serious adverse events
SLL—small lymphocytic lymphoma
t½—half-life
ULN—upper limit of normal
WBC—white blood cells
ZAP-70—zeta chain-associated T-cell receptor protein kinase 70 kDa

BIBLIOGRAPHY

1. Bundgaard (1985) *Design of Prodrugs*, (Elsevier);
2. Bundgaard et al. (1991) *A Textbook of Drug Design and Development*, Chapter 5, (Harwood Academic Publishers).
3. Byrd et al. (2013)*N Engl J Med*, 369:32-42.
4. Cheson et al. (1996) *Blood*, 87:4990-4997.
5. Cheson et al. (2012), *J Clin Oncol*, 30:2820-2822.
6. Ilallek et al. (2008) *Blood*, 111:5446-5456.
7. Thurmes et al. (2008) *Leuk Lymphoma*, 49:49-56.
8. Wermuth et al. (1996) *The Practice of Medicinal Chemistry*, Chapter 31 (Academic Press);

The claims defining the invention are as follows:

1. A method for treating chronic lymphocytic leukemia (CLL) in a patient comprising the step of administering effective amounts of (i) a compound which induces egress of CLL cells from lymph node or bone marrow or a pharmaceutically acceptable salt, solvate, stereoisomer or prodrug thereof; and (ii) a compound of Formula (I):

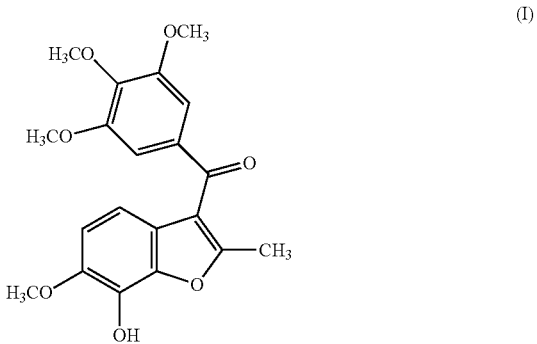 [SMILES: COc1cc(C(=O)c2c(C)oc3c(O)c(OC)ccc23)cc(OC)c1OC]

or a pharmaceutically acceptable salt, solvate or prodrug thereof, in either order or simultaneously.

2. The method of claim 1 wherein the patient is a human subject.

3. The method of claim 1 wherein the compound which induces egress of CLL cells from lymph node or bone marrow is ibrutinib.

4. The method of claim 3 wherein the effective amounts are administered in cycles comprising one of ibrutinib or a compound of Formula (I) in a first cycle; and the other of ibrutinib and/or a compound of Formula (I) and ibrutinib in a second cycle and such respective cycles as necessary for amelioration of symptoms of CLL in the subject.

5. The method of claim 4 wherein the amount of ibrutinib is from 200 to 800 mg daily.

6. The method of claim 4 wherein the effective amount of the compound of Formula (1) is from 1 to 20 mg/m$^2$.

7. The method of claim 1 wherein the compounds are administered by oral or parenteral administration.

8. The method of claim 1 wherein the compounds are co-administered simultaneously or sequentially with another anti-cancer agent.

9. The method of claim 1 wherein the patient is selected for treatment based on clinical parameters including age, level of progression of the disease, and/or other complicating ailments.

10. The method of claim 9 wherein the patient exhibits relapsed or refractory CLL.

11. The method of claim 1 wherein the compound of Formula (I) is:

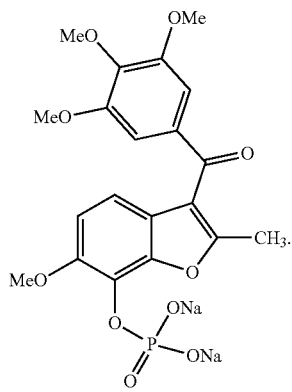

12. A composition comprising a compound which induces egress of CLL cells from lymph node or bone marrow or a pharmaceutically acceptable salt, solvate, stereoisomer or prodrug thereof; and a compound of Formula (I):

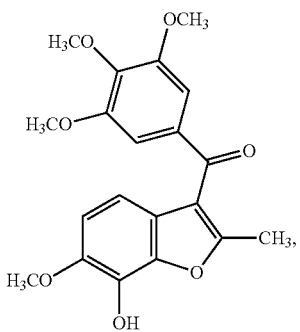

(I)

or a pharmaceutically acceptable salt, solvate or prodrug thereof; for use in treating CLL in a patient.

13. The composition of claim 12 wherein the patient is a human.

14. The composition of claim 13, wherein the compound which induces egress of CLL cells from lymph node or bone marrow is ibrutinib.

15. The composition of claim 13 wherein the human has relapsed or refractory CLL.

16. The composition of claim 12 wherein the composition further comprises another anti-cancer agent.

17. The composition of claim 12 wherein the compound of Formula (I) is:

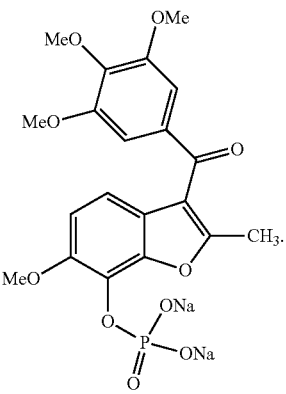

18. A pharmaceutical kit for treating CLL comprising ibrutinib or a pharmaceutically acceptable salt, solvate, stereoisomer or prodrug thereof; and a compound of Formula (I):

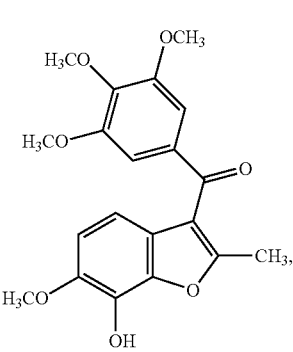

(I)

or a pharmaceutically acceptable salt, salute or prodrug thereof;
together with instructions for use.

19. The method of claim 1 wherein the compound of Formula (I) is:

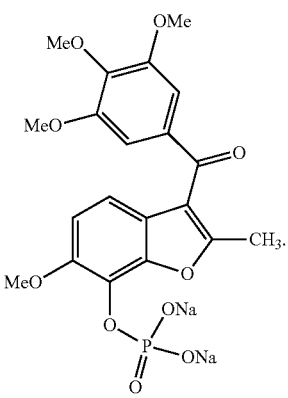

* * * * *